(12) United States Patent
Ziraknejad et al.

(10) Patent No.: US 11,007,020 B2
(45) Date of Patent: May 18, 2021

(54) METHODS AND SYSTEMS FOR TOUCHLESS CONTROL OF SURGICAL ENVIRONMENT

(71) Applicant: NZ TECHNOLOGIES INC., Vancouver (CA)

(72) Inventors: Nima Ziraknejad, North Vancouver (CA); Pranav Saxena, Vancouver (CA); Anshul Porwal, Surrey (CA); Nameet Kumar, New Westminster (CA)

(73) Assignee: NZ Technologies Inc., Vancouver (CA)

( * ) Notice: Subject to any disclaimer, the term of this patent is extended or adjusted under 35 U.S.C. 154(b) by 0 days.

(21) Appl. No.: 16/535,040

(22) Filed: Aug. 7, 2019

(65) Prior Publication Data

US 2020/0038120 A1 Feb. 6, 2020

Related U.S. Application Data

(63) Continuation of application No. PCT/CA2018/050185, filed on Feb. 16, 2018.
(Continued)

(51) Int. Cl.
*G06F 3/0482* (2013.01)
*A61B 34/00* (2016.01)
(Continued)

(52) U.S. Cl.
CPC .............. *A61B 34/25* (2016.02); *G06F 3/012* (2013.01); *G06F 3/017* (2013.01); *G06F 3/0482* (2013.01);
(Continued)

(58) Field of Classification Search
CPC ......... A61B 34/25; A61B 34/20; A61B 34/30; A61B 2090/365; A61B 2090/368;
(Continued)

(56) References Cited

U.S. PATENT DOCUMENTS

| 8,230,367 B2 | 7/2012 | Bell et al. | |
| 2002/0068862 A1* | 6/2002 | Kleiman | A61B 6/467 600/407 |

(Continued)

OTHER PUBLICATIONS

Justin H. Tan et al., "Informatics in Radiology: Developing a Touchless User Interface for Intraoperative Image Control during Interventional Radiology Procedures". Radiographics., vol. 33, No. 2, Apr. 30, 2013 (Apr. 30, 2013), pp. E61-E70.
(Continued)

*Primary Examiner* — Jeanette J Parker
(74) *Attorney, Agent, or Firm* — Todd A. Rattray; Oyen Wiggs Green & Mutala LLP

(57) ABSTRACT

A method facilitates touchless control of medical equipment devices in an OR. The method involves: providing a three-dimensional control menu, which comprises a plurality of menu items selectable by the practitioner by one or more gestures made in a volumetric spatial region corresponding to the menu item; displaying an interaction display unit (IDU) image corresponding to the three-dimensional control menu to provide indicia of any selected menu items; estimating a line of sight of a practitioner; and when the estimated line of sight is directed within a first spatial range around a first medical equipment device, determining that the practitioner is looking at the first medical equipment device. Then the method involves providing a first device-specific three-dimensional control menu displaying a first device-specific IDU image.

25 Claims, 14 Drawing Sheets

Related U.S. Application Data

(60) Provisional application No. 62/460,736, filed on Feb. 17, 2017.

(51) Int. Cl.
| | |
|---|---|
| *G06F 3/01* | (2006.01) |
| *G06F 3/0481* | (2013.01) |
| *G06F 3/0484* | (2013.01) |
| *G06F 3/14* | (2006.01) |
| *A61B 34/20* | (2016.01) |
| *A61B 34/30* | (2016.01) |
| *A61B 90/00* | (2016.01) |
| *A61B 90/50* | (2016.01) |
| *A61B 17/00* | (2006.01) |

(52) U.S. Cl.
CPC ........ *G06F 3/0484* (2013.01); *G06F 3/04815* (2013.01); *G06F 3/1423* (2013.01); *A61B 34/20* (2016.02); *A61B 34/30* (2016.02); *A61B 2017/00207* (2013.01); *A61B 2017/00216* (2013.01); *A61B 2090/365* (2016.02); *A61B 2090/368* (2016.02); *A61B 2090/372* (2016.02); *A61B 2090/502* (2016.02)

(58) Field of Classification Search
CPC ........ A61B 2090/372; A61B 2090/502; A61B 2017/00207; A61B 2017/00216; A61B 90/50; A61B 34/00; A61B 90/30; A61B 2090/376; A61B 90/98; A61B 2034/2048; A61B 2034/2055; A61B 2034/2065; A61B 2090/366; G06F 3/012; G06F 3/017; G06F 3/04815; G06F 3/0482; G06F 3/0484; G06F 3/1423; G06F 3/013; G06F 3/048; G06F 3/011; G06F 3/016; G06F 3/0487

See application file for complete search history.

(56) References Cited

U.S. PATENT DOCUMENTS

| | | |
|---|---|---|
| 2008/0263479 A1 | 10/2008 | Bloem et al. |
| 2009/0021475 A1 | 1/2009 | Steinle et al. |
| 2009/0077504 A1 | 3/2009 | Bell et al. |
| 2009/0228841 A1 | 9/2009 | Hildreth |
| 2011/0181553 A1 | 7/2011 | Brown et al. |
| 2012/0249741 A1 | 10/2012 | Maciocci et al. |
| 2013/0007668 A1 | 1/2013 | Liu et al. |
| 2013/0007672 A1 | 1/2013 | Taubman |
| 2013/0076620 A1 | 3/2013 | Fukano |
| 2013/0265219 A1 | 10/2013 | Sato |
| 2013/0321346 A1 | 12/2013 | Tyler et al. |
| 2014/0049465 A1 | 2/2014 | Tremaine et al. |
| 2014/0085185 A1* | 3/2014 | Sarwar ................. G06F 3/0304 345/156 |
| 2014/0177909 A1 | 6/2014 | Lin et al. |
| 2014/0195983 A1 | 7/2014 | Du et al. |
| 2015/0208019 A1 | 7/2015 | Stewart et al. |
| 2015/0212576 A1 | 7/2015 | Ambrus et al. |
| 2015/0279110 A1* | 10/2015 | Kimura .................. G06F 3/012 345/633 |
| 2016/0116995 A1* | 4/2016 | Wilson ................ H04N 13/128 345/157 |
| 2016/0364003 A1* | 12/2016 | O'Brien ............... G03H 1/0005 |
| 2017/0120749 A1* | 5/2017 | Dias ........................ G08B 21/06 |
| 2017/0285739 A1* | 10/2017 | Aaron ................. G06F 3/04895 |
| 2017/0347979 A1* | 12/2017 | Fehre ..................... G16H 30/20 |
| 2018/0007328 A1* | 1/2018 | Kursula ............... H04N 9/3194 |
| 2019/0099222 A1* | 4/2019 | Nahum ................. G16H 40/60 |
| 2019/0167370 A1* | 6/2019 | Olson ................. G06K 9/00335 |
| 2019/0298481 A1* | 10/2019 | Rosenberg ............... G06T 7/70 |

OTHER PUBLICATIONS

Wachs et al., "A gesture-based tool for sterile browsing of radiology images." Journal of the American Medical Informatics Association vol. 15, No. 3, 321-323, May/Jun. 2008 (Jun. 2008).

Wachs et al., "Real-time hand gesture interface for browsing medical images." International Journal of Intelligent Computing in Medical Sciences & Image Processing, vol. 1. No. 3, 175-185. Mar. 3, 2007.

Ahmed et al., "Geometric Correction for Uneven Quadric Projection Surfaces Using Recursive Subdivision of Bézier Patches". ETRI Journal, vol. 35, No. 6, Dec. 2013, pp. 1115-1125.

Andriole et al., "Optimizing Analysis, Visualization, and Navigation of Large Image Data Sets: One 5000-Section CT Scan Can Ruin Your Whole Day". Department of Radiology, vol. 259: No. 2—May 2011, pp. 346-362.

Breuer et al., "Hand Gesture Recognition With a Novel IR Time-of-Flight Range Camera—A Pilot Study". Mirage 2007, LNCS 4418, pp. 247-260.

Johnson et al., "Exploring the Potential for Touchless Interaction in Image-Guided Interventional Radiology". CHI 2011 Session: Doctor-Patient Care, May 7-12, 2011, pp. 3323-3332.

Van den Bergh et al., "Haarlet-based Hand Gesture Recognition for 3D Interaction". Competence Center of Digital Design Modeling (DDM) at ETH Zurich. 2009, 8 pages.

Ziraknejad, et al., "The Effect of Time-of-Flight Camera Integration Time on Vehicle Driver Head Pose Tracking Accuracy". 2012 IEEE International Conference on Vehicular Electronics and Safety, Jul. 24-27, 2012.

"Natural User Interfaces for Healthcare". Website found at: http://www.tedcas.com; web page archive May 18, 2014.

"Take Control of Your Operating Room". Website found at: http://www.gestsure.com; web page archive Jul. 29, 2014.

\* cited by examiner

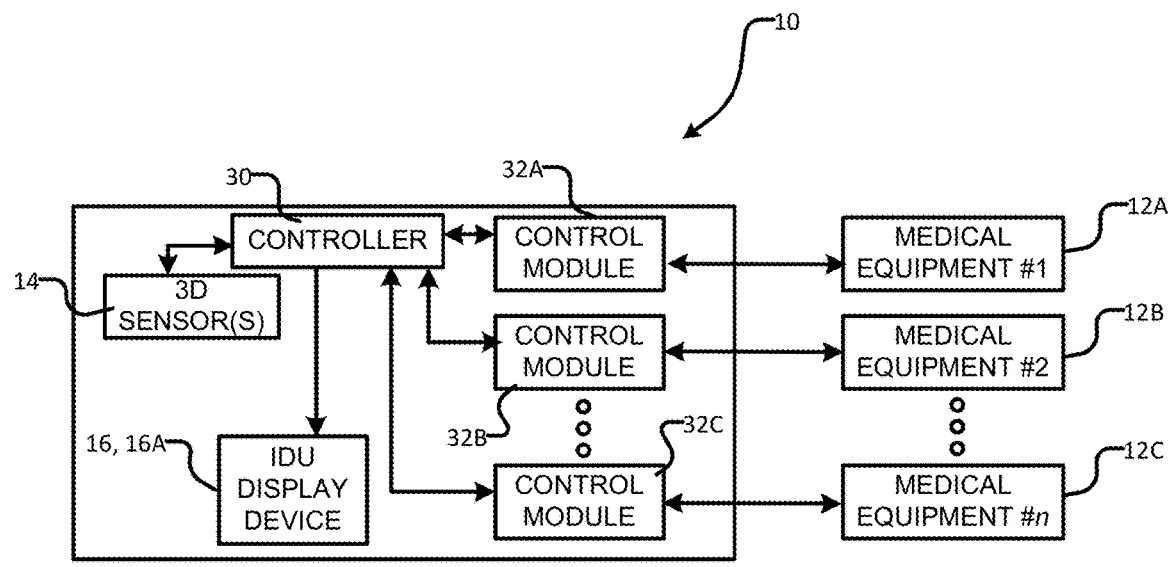
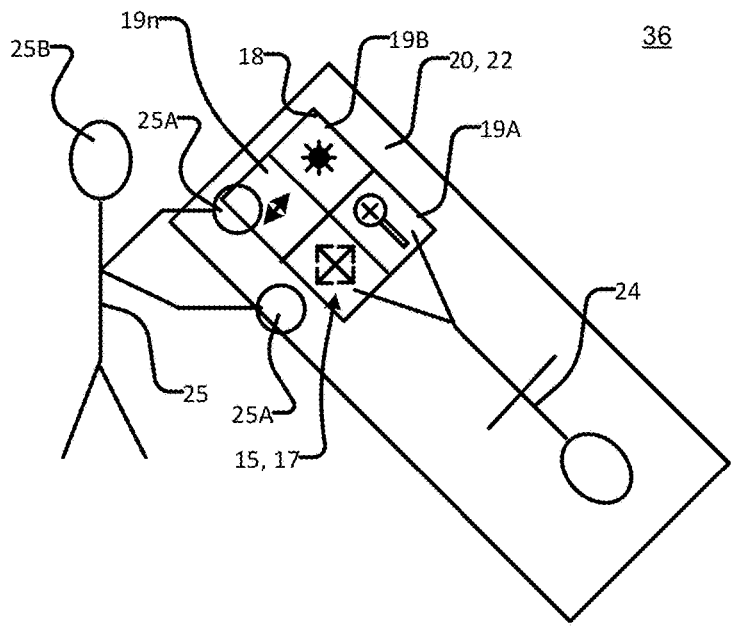
FIGURE 1A

METHODS AND SYSTEMS FOR TOUCHLESS CONTROL OF SURGICAL ENVIRONMENT

RELATED APPLICATIONS

This application is a continuation of Patent Cooperation Treaty (PCT) application No. PCT/CA2018/050185 which has an international filing date of 16 Feb. 2018 and which, in turn, claims priority from, the benefit under 35 USC § 119(e) of, U.S. application No. 62/460,736 filed 17 Feb. 2017. This application describes and/or claims subject matter that is related to the subject matter disclosed and/or claimed in PCT application No. PCT/CA2015/050764 filed 13 Aug. 2015 and PCT application No. PCT/IB2016/056228 filed 17 Oct. 2016 (together, the "Related PCT Applications"). PCT application No. PCT/CA2018/0500185, U.S. application No. 62/460,736 and the Related PCT Applications are hereby incorporated herein by reference in their entireties for all purposes.

FIELD

The technology disclosed herein relates to methods and systems for controlling or otherwise interacting with equipment, tools and/or the like in a medical (e.g. surgical) environment.

BACKGROUND

There is a general desire for medical practitioners (e.g. surgeons, interventional radiologists, nurses, medical assistants, other medical technicians and/or the like) to control or otherwise interact with medical equipment, tools and/or the like in a medical (e.g. surgical) environment.

By way of non-limiting example, the Related PCT Applications describe the desirability for medical practitioners to interact with information systems which provide medical information (e.g. images of the patient's body and/or organs) that may be germane to the procedure being performed. Such desired medical information may include, by way of non-limiting example, radiological images, angiography images, other forms of images of the patient's body, other information relevant to a patient undergoing the medical procedure, other information relevant to the procedure itself, other information related to the condition being treated and/or the like. Such desired medical information may be procured prior to performing the procedure and/or during performance of the procedure and may allow medical practitioners to formulate or alter their therapeutic plan during image-guided medical procedures.

However, the desirability of controlling or otherwise interacting with medical equipment, tools and/or the like in a medical (e.g. surgical) environment is not limited to information systems. There is a desire to control other types of medical equipment, tools and/or the like in surgical environments. By way of non-limiting example, it can be desirable to control the pose (i.e. orientation and position) of an adjustable patient bed (e.g. to tilt the patient's body); the brightness of a light source; the directionality of a spotlight or working light; the information displayed by diagnostic equipment (vital signs monitors); the rate of infusion of an intra-venous drug delivery system and/or the like.

SUMMARY

This invention has a number of aspects. These aspects may be applied individually or in any combinations. Some aspects provide systems and methods for touchlessly controlling medical equipment.

One aspect of the invention provides a method for touchless control of one of more medical equipment devices in an operating room. The method comprises providing a three-dimensional control menu, the three-dimensional control menu comprising a plurality of menu items, each menu item selectable by the practitioner by one or more gestures made by the practitioner in a volumetric spatial region corresponding to the menu item; displaying an interaction display unit (IDU) image corresponding to the three-dimensional control menu, the IDU image providing indicia of any one or more selected menu items; estimating a line of sight of a practitioner; when the estimated line of sight is directed within a first spatial range around a first medical equipment device, determining that the practitioner is looking at the first medical equipment device and wherein, after determining that the practitioner is looking at the first medical equipment device: providing the three-dimensional control menu comprises providing a first device-specific three-dimensional control menu comprising first device-specific menu items which, when selected, result in delivering corresponding operational commands to the first medical equipment device to control operation of the first medical equipment device; and displaying the IDU image corresponding to the three-dimensional control menu comprises displaying a first device-specific IDU image comprising graphics or text corresponding to the first device-specific menu items.

Another aspect of the invention provides a system for touchless control of one or more medical equipment devices. The system comprises a 3D optical sensor connected for detecting one or more gestures made by a practitioner in a sensing volume of the sensor; a controller connected to receive 3D optical data from the 3D optical sensor and configured to provide a three-dimensional control menu, the three-dimensional control menu comprising a plurality of menu items, each menu item selectable by the practitioner by one or more gestures made by the practitioner in a volumetric spatial region corresponding to the menu item and detected by the controller based on the 3D optical data; an IDU display for displaying an IDU image corresponding to the three-dimensional control menu, the IDU image providing indicia of any one or more selected menu items. The controller is further configured, based on input from one or more sensors, to estimate a line of sight of a practitioner. When the estimated line of sight is directed within a first spatial range around a first medical equipment device, the controller is configured to determine that the practitioner is looking at the first medical equipment device and wherein, after determining that the practitioner is looking at the first medical equipment device, the controller is configured to: provide a first device-specific three-dimensional control menu comprising first device-specific menu items which, when selected, result in delivering corresponding operational commands to the first medical equipment device to control operation of the first medical equipment device; and cause the IDU display to display a first device-specific IDU image comprising graphics or text corresponding to the first device-specific menu items.

Another aspect of the invention provides a method for touchless control of one or more medical equipment devices in an operating room. The method comprises providing a three-dimensional control menu, the three-dimensional control menu comprising a plurality of menu items, each menu item selectable by the practitioner by one or more gestures made by the practitioner in a volumetric spatial region corresponding to the menu item; displaying an IDU image corresponding to the three-dimensional control menu, the IDU image providing indicia of any one or more selected menu items; wherein selection of any particular one of the menu items results in delivering a corresponding operational command to at least one of the one or more medical equipment devices to control operation of the at least one of the one or more medical equipment devices; estimating at least one of a location of a head of the practitioner and an orientation of the head of the practitioner; and adjusting display of the IDU image based at least in part on the at least one of the estimated location of the head of the practitioner and the estimated orientation of the head of the practitioner.

One aspect of the invention provides a system for touchless control of one or more medical equipment devices in an operating room. The system comprises a 3D optical sensor connected for detecting one or more gestures made by a practitioner in a sensing volume of the sensor; a controller connected to receive 3D optical data from the 3D optical sensor and configured to provide a three-dimensional control menu, the three-dimensional control menu comprising a plurality of menu items, each menu item selectable by the practitioner by one or more gestures made by the practitioner in a volumetric spatial region corresponding to the menu item; and an IDU display for displaying an IDU image corresponding to the three-dimensional control menu, the IDU image providing indicia of any one or more selected menu items. The controller is configured to determine selection of any particular one of the menu items and to deliver a corresponding operational command to at least one of the one or more medical equipment devices to control operation of the at least one of the one or more medical equipment devices. The controller is configured, based on input from one or more sensors, to estimate at least one of a location of a head of the practitioner and an orientation of the head of the practitioner and to adjust the display of the IDU image by the IDU display based at least in part on the at least one of the estimated location of the head of the practitioner and the estimated orientation of the head of the practitioner.

Another aspect of the invention provides a method for touchless control of one or more medical equipment devices in an operating room. The method comprises providing a three-dimensional control menu, the three-dimensional control menu comprising a plurality of menu items, each menu item selectable by a practitioner by one or more gestures made by the practitioner in a volumetric spatial region corresponding to the menu item; projecting an IDU image corresponding to the three-dimensional control menu onto a non-planar projection surface, the IDU image providing indicia of any one or more selected menu items; wherein selection of any particular one of the menu items results in delivering a corresponding operational command to at least one of the one or more medical equipment devices to control operation of the at least one of the one or more medical equipment devices; obtaining an estimate of a profile of the non-planar projection surface; estimating a viewing vector of the practitioner to the projection surface; and pre-adjusting the IDU image prior to projecting the IDU image, the pre-adjustment based at least in part on the estimated profile of the non-planar projection surface and the estimated viewing vector.

One aspect of the invention provides a system for touchless control of one or more medical equipment devices in an operating room. The system comprises a 3D optical sensor connected for detecting one or more gestures made by a practitioner in a sensing volume of the sensor; a controller connected to receive 3D optical data from the 3D optical sensor and configured to provide a three-dimensional control menu, the three-dimensional control menu comprising a plurality of menu items, each menu item selectable by the practitioner by one or more gestures made by the practitioner in a volumetric spatial region corresponding to the menu item and detected by the controller based on the 3D optical data; an IDU display for displaying an IDU image corresponding to the three-dimensional control menu onto a non-planar projection surface, the IDU image providing indicia of any one or more selected menu items, wherein selection of any particular one of the menu items results in delivering a corresponding operational command to at least one of the one or more medical equipment devices to control operation of the at least one of the one or more medical equipment devices. The controller is configured, based on input from one or more sensors, to estimate a profile of the non-planar projection surface. The controller is configured, based on input from one or more sensors, to estimate a viewing vector of the practitioner to the non-planar projection surface. The IDU display is configured to pre-adjust the IDU image prior to projecting the IDU image, the pre-adjustment based at least in part on the estimated profile of the non-planar projection surface and the estimated viewing vector.

One aspect of the invention provides a method for touchless control of one or more medical equipment devices in an operating room (OR). The method comprises providing a three-dimensional control menu, the three-dimensional control menu comprising a plurality of menu items, each menu item selectable by the practitioner by one or more gestures made by the practitioner in a volumetric spatial region corresponding to the menu item; projecting an IDU image corresponding to the three-dimensional control menu onto a non-planar projection surface, the IDU image providing indicia of any one or more selected menu items; wherein selection of any particular one of the menu items results in delivering a corresponding operational command to at least one of the one or more medical equipment devices to control operation of the at least one of the one or more medical equipment devices; providing one or more 3D optical sensors which are mounted to a robotic positioning system for at least one of moving and orienting the one or more 3D optical sensors; and performing at least one of moving and orienting the robotic positioning system and capturing 3D optical data corresponding to a region of interest in the OR and processing the captured 3D optical data to locate and identify the one or more medical equipment devices in the operating room that are controllable using the three-dimensional control menu.

One aspect of the invention provides a system for touchless control of one or more medical equipment devices in an operating room (OR). The system comprises one or more 3D optical sensors connected for detecting one or more gestures made by a practitioner in a sensing volume of the one or more 3D optical sensors, the one or more 3D optical sensors mounted on a robotic positioning system for at least one of moving or orienting the one or more 3D optical sensors; a controller connected to receive 3D optical data from the 3D optical sensor and configured to provide a three-dimensional control menu, the three-dimensional control menu comprising a plurality of menu items, each menu item selectable by the practitioner by one or more gestures made by the practitioner in a volumetric spatial region corresponding to the menu item and detected by the controller based on the 3D optical data; an IDU display for displaying an IDU image corresponding to the three-dimensional control menu onto a non-planar projection surface, the IDU image providing indicia of any one or more selected menu items, wherein selection of any particular one of the menu items results in delivering a corresponding operational command to at least one of the one or more medical equipment devices to control operation of the at least one of the one or more medical equipment devices. The one or more 3D optical sensors are configured to capture 3D optical data corresponding to a region of interest in the OR and process the captured 3D optical data to locate and identify the one or more medical equipment devices in the OR that are controllable using the three-dimensional control menu.

One aspect of the invention provides a method for touchless control of one or more medical equipment devices in an operating room (OR). The method comprises providing a three-dimensional control menu, the three-dimensional control menu comprising a plurality of menu items, each menu item selectable by the practitioner by one or more gestures made by the practitioner in a volumetric spatial region corresponding to the menu item; projecting an IDU image corresponding to the three-dimensional control menu onto a non-planar projection surface, the IDU image providing indicia of any one or more selected menu items; wherein selection of any particular one of the menu items results in delivering a corresponding operational command to at least one of the one or more medical equipment devices to control operation of the at least one of the one or more medical equipment devices; providing an IDU display for projecting the IDU image, the IDU display mounted to a robotic positioning system for at least one of moving and orienting the IDU display; performing at least one of moving and orienting the robotic positioning system, and projecting the IDU image onto a first surface; and after receiving an indication that the first surface is undesirable or determining that a practitioner has moved within the OR, performing at least one of moving and orienting the robotic positioning system, and projecting the IDU image onto a second surface.

One aspect of the invention provides a system for touchless control of one or more medical equipment devices in an operating room (OR). The system comprises a 3D optical sensor connected for detecting one or more gestures made by a practitioner in a sensing volume of the sensor; a controller connected to receive 3D optical data from the 3D optical sensor and configured to provide a three-dimensional control menu, the three-dimensional control menu comprising a plurality of menu items, each menu item selectable by the practitioner by one or more gestures made by the practitioner in a volumetric spatial region corresponding to the menu item and detected by the controller based on the 3D optical data; an IDU display for displaying an IDU image corresponding to the three-dimensional control menu onto a non-planar projection surface, the IDU image providing indicia of any one or more selected menu items, the IDU display mounted to a robotic positioning system for at least one of moving and orienting the IDU display. Selection of any particular one of the menu items results in delivering a corresponding operational command to at least one of the one or more medical equipment devices to control operation of the at least one of the one or more medical equipment devices. The IDU display is configured to project the IDU image onto a first surface. The controller is configured to receive an indication that the first surface is undesirable or determining that a practitioner has moved within the OR, and upon receiving such an indication or making such a determination, the IDU display is configured to project the IDU image onto a second surface.

Further aspects of the invention and features of specific embodiments of the invention are described herein.

BRIEF DESCRIPTION OF THE DRAWINGS

The accompanying drawings illustrate non-limiting example embodiments of the invention.

FIGS. 1A-1C schematically depict systems for touchless control of medical equipment, according to example embodiments of the invention.

DETAILED DESCRIPTION

Figure 1B:
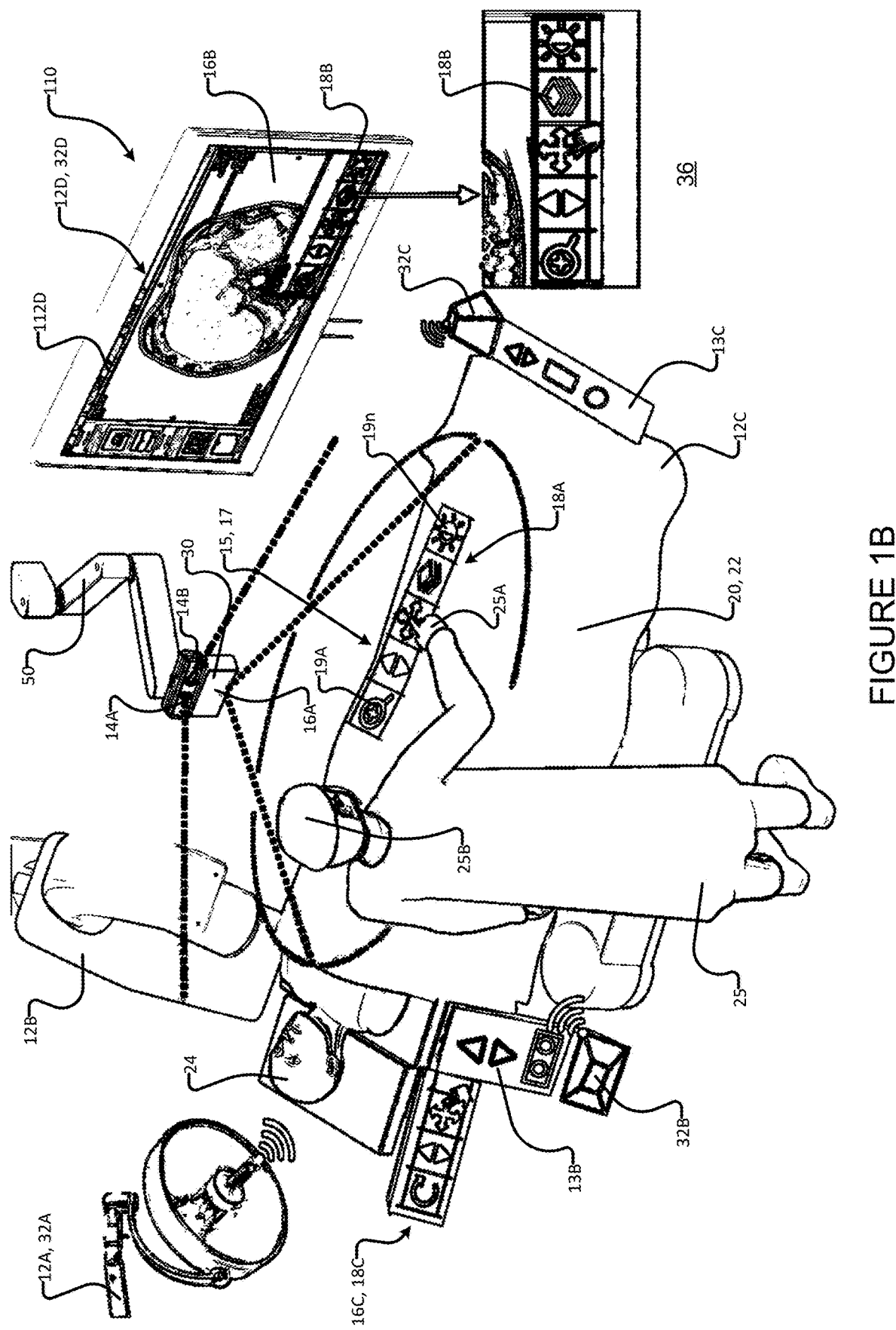

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Aspects of the invention provide systems and methods for touchless control or other interaction with medical equipment, tools and/or the like in a medical (e.g. surgical) environment using hand motions (e.g. gestures and/or the like). Medical practitioners interact with one or more adjustable menus defined in volumetric spatial regions located near to (e.g. within arm's reach of) the practitioner. The space in which the one or more menus are located may be referred to as the workspace and the one or more menus may be referred to as the 3D control menus. A practitioner may interact with the 3D control menu (e.g. to select a menu item or to otherwise interact with the 3D control menu) using hand motions based on the configuration (gestures like pointing, finger-tapping, etc.), location, or movement of a practitioner's hand(s) and/or finger(s). The 3D control menu comprises a plurality of volumetric spatial regions (each such spatial region corresponding to a menu item, for example) within which the practitioner's hand(s) may perform suitable hand motion(s) for interaction with the 3D control menu. The 3D control menu may be implemented by a suitably configured controller which receives data from at least one 3D optical sensor and performs a machine vision algorithm that processes optical data received from the 3D optical sensor and interprets that optical data as interaction of the practitioner with the 3D control menu. The controller may be additionally connected, in communication with or otherwise configured to control medical equipment based on the practitioner's interaction with the 3D control menu.

Typically, a practitioner's interaction with the 3D control menu will involve selection of one or more menu items which may in turn result in the delivery of suitable control commands to medical equipment. As discussed above, menu items may correspond to volumetric spatial regions (rather than to physical objects). Consequently, it can be desirable for the practitioner to receive some feedback to indicate that they have effectively selected or otherwise interacted with a menu item. To aid the practitioner's interaction with the 3D control menu, particular embodiments of the invention comprise an interaction display unit (IDU) which displays a visual depiction of the 3D control menu's current configuration (including, for example, displayed indications of any selection, or other interaction, with menu items) to provide useful real-time feedback to notify the practitioner about selections and menu interactions. The IDU may be embodied in a number of different ways. By way of non-limiting example the IDU may comprise a projector which may be used to project the 3D control menu on a suitable surface (e.g. an operating table which may or may not have a patient located thereon, the practitioner's hand, an operating room side table and/or the like). As another non-limiting example, the IDU may comprise a physical display with a depiction of the 3D control menu and a depiction of the practitioner's hand or some other suitable pointing device graphic over the menu. Such a display may be integrated within an existing display used in the medical procedure being performed or may be separately implemented on an independent display. The display may optionally be implemented in wearable technology such as smart glasses, smart watches, augmented/virtual reality headsets and/or the like. In a still further non-limiting example, the IDU comprises one or more projectors that are part of an augmented reality headset for virtual depictions of the 3D control menu. Each of these exemplary IDU formats can be configured to provide indicia which inform the practitioner of selected menu items and/or positioning of their hand(s) and/or finger(s) within or relative to the workspace.

In some embodiments, the IDU may additionally or alternatively display medical image data, such as radiological images, angiography images, or other images of the patient's body. Such medical image data could alternatively be displayed on a display separate from the IDU (e.g. on a separate projector screen, television, monitor, or the like).

System Overview

FIG. 1A schematically depicts a system 10 for touchless control of medical equipment 12A, 12B, 12C (collectively and individually, medical device 12 or equipment 12) according to a particular embodiment. System 10 comprises one or more 3D optical sensor unit(s) 14 which may be used to obtain 3D optical information about objects in workspace 15, including, in particular the body parts of practitioner 25 (e.g. hand(s) 25A, finger(s) and/or head 25B of practitioner 25). By way of non-limiting example, 3D optical sensor unit(s) 14 may comprise stereo cameras, Time of Flight (ToF) cameras, LIDAR sensors and/or the like. System 10 also comprises an IDU display device 16 which provides a visual guide and feedback to practitioner 25, as discussed above. In the particular example embodiment shown in FIG. 1A, IDU display device 16 comprises a projector 16A, which projects an IDU image 18 corresponding to the 3D control menu onto the surface 20 of an operating table 22 on which a patient 24 is located. In other embodiments, other forms of IDU display device may display IDU image in different manners (e.g. in a physical display or as a virtual reality object) as described above.

System 10 also comprises a system controller 30 (also referred to as controller 30). System controller 30 may be implemented by, or may otherwise comprise, one or more programmable data processes suitably configured using applicable software, as described elsewhere herein. In the illustrated FIG. 1A embodiment, IDU display device 16, 3D optical sensor(s) 14 and controller 30 work together to provide a 3D control menu 17 in workspace 15 located just above surface 20 of operating table 22. Control menu 17 comprises one or more menu items 19A, 19B . . . 19n (collectively, and individually menu items 19), each menu item 19 corresponding to a volumetric spatial region in workspace 15. Practitioner 25 may interact with 3D control menu 17 (e.g. to select a menu item 19 or to otherwise interact with the 3D control menu 17) using hand motions based on the configuration (gestures like pointing, finger-tapping, etc.), location, or movement of a practitioner's hand(s) and/or finger(s).

System controller 30 also uses 3D optical data received from 3D optical sensor(s) 14 to control medical equipment 12 via control modules 32A, 32B, 32C (collectively and individually, control modules 32). Control modules 32 perform the task of interfacing between controller 30 and various types of medical equipment 12. Specifically, control modules 32 receive commands from controller 30 and use various forms of communications interface(s) and protocol(s) to provide particular commands to equipment 12 to thereby control or otherwise interact with equipment 12. By way of non-limiting example, control modules 32 may comprise Bluetooth communications protocols, USB dongles, LAN communications interfaces, WiFi communications interfaces, data communication protocols/means (e.g. serial com interfaces) and/or the like. In some embodiments, some or all of control modules 32 may be implemented in whole or in part by controller 30.

System 10 (and methods implemented by system 10) allow practitioner 25 to touchlessly interact with and control multiple devices and equipment 12 located inside operating room 36 or remote to operating room 36. Non-limiting examples of such devices and equipment 12 include a medical image display device such as a Picture Archiving and Communication System (PACS) workstation, intraoperative radiology image workstation, surgical lights, a patient bed (operating table), patient diagnostic equipment, a radiology image acquisition system, fluoroscopy equipment (e.g. a C-Arm), other types of medical imaging systems, drug delivery systems, robotic surgical equipment, robotic surgical assistance equipment, control panels for the control of other medical equipment and/or the like. One specific type of equipment 12 which may be controlled by system 10 is a control interface (e.g. a GUI, a touch panel interface and/or the like) for controlling other medical equipment. Currently, many such devices 12 are outside the direct control of practitioner 25 during a procedure, because they are not operable while remaining sterile. Using system 10, medical practitioner 25 would no longer need to scrub out of the sterile environment in which the procedure is being performed or communicate with technicians located outside of the sterile environment to control such devices 12 nor would medical practitioner 25 need to communicate with or delegate tasks to a technician or nurse inside the sterile environment. Removing such distractions may thus aid practitioner 25 in maintaining focus on the procedure being performed.

FIG. 1B schematically depicts a system 110 for touchless control of medical equipment 12 according to another example embodiment. System 110 is similar in many respects to system 10 of FIG. 1A and similar reference numerals are used to refer to similar components. System 110 comprises two 3D optical sensors 14A, 14B, one of which is configured to sense 3D information in workspace 15 (including the locations of the hands 25A of practitioner 25) and the other one of which is configured to sense 3D information corresponding to the location of the head 25B of practitioner 25. System 110 also comprises three IDU display devices 16A, 16B, 16C (collectively and individually IDU display devices 16) which display IDU images 18A, 18B, 18C (collectively and individually IDU images 18). In practice, not all of IDU display devices 16 are necessary, but a number of IDU display devices 16 and their corresponding IDU images 18 are shown in FIG. 1B for the purpose of explanation. In the example embodiment shown in FIG. 1B, IDU display device 16A comprises a projector 16A, which projects an IDU image 18A corresponding to the 3D control menu 17 and menu items 19 onto the surface 20 of an operating table 22 on which a patient 24 is located. In the example embodiment shown in FIG. 1B, IDU display device 16B comprises a display 16B (which is actually a piece of medical equipment 12 used to display medical images), wherein an IDU image 18B corresponding to the 3D control menu is overlaid on the display image. In the example embodiment shown in FIG. 1B, IDU display device 16C comprises a dedicated IDU display 16C which displays an IDU image 18C corresponding to the 3D control menu.

To properly locate and orient IDU images 18, it may be desirable to establish a world coordinate frame in physical space. Such a coordinate frame may provide the coordinate frame to which all position and orientation data are referenced. The world coordinate frame may be provided by placing one of 3D optical sensors 14A or 14B, or another suitable sensor or marker, in a known physical position such as at the base of robotic arm 50, on a camera projector mount, at the base of operating table 22, and/or the like. This physical position may then be defined as the origin of the coordinate frame, for proper position referencing of all IDU images, 3D control menu components, and medical equipment in the room.

System 110 also comprises a system controller 30 (also referred to as controller 30), which receives 3D optical data from 3D optical sensors 14A, 14B and uses such data to control medical equipment 12 via control modules 32. In the illustrated example embodiment of FIG. 1B, medical equipment 12 being controlled includes surgical light 12A, C-Arm 12B, bed 12C and medical image display 12D, which are respectively interfaced by control modules 32A, 32B, 32C, 32D.

Figure 1C:
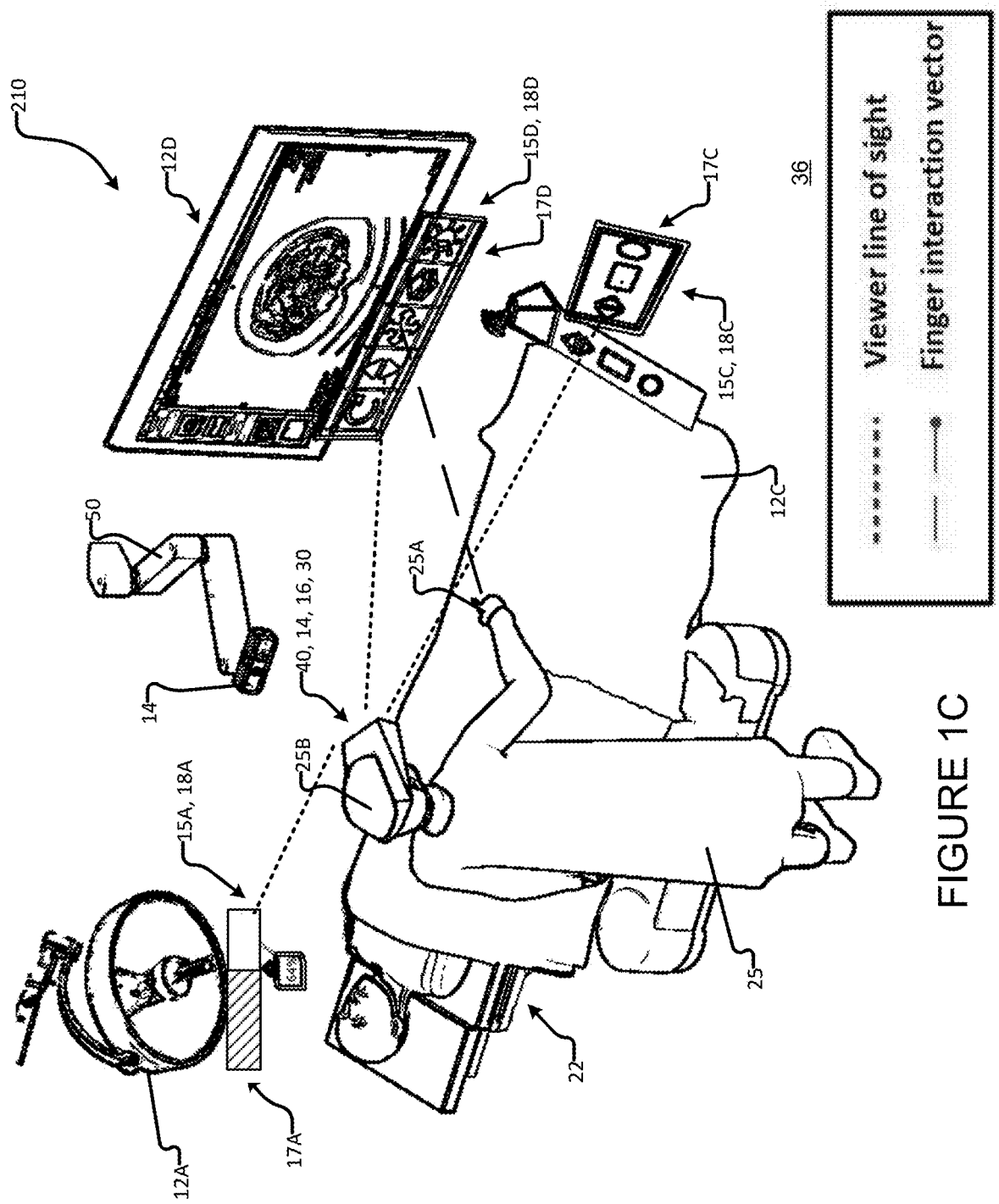

FIG. 1C schematically depicts a system 210 for touchless control of medical equipment 12 according to another example embodiment. System 210 is similar in many respects to systems 10, 110 of FIGS. 1A, 1B and similar reference numerals are used to refer to similar components. System 210 differs from systems 10, 110 in that a number of the components of system 210 are integrated into an augmented reality (AR) headset 40—also referred to as AR goggles 40, virtual reality (VR) headset 40 or VR goggles 40. Specifically, referring to FIG. 1A, 3D optical sensor(s) 14, IDU display device 16 and optionally system controller 30 and any components of control modules 32 implemented by system controller 30 may be integrated into AR headset 40. The functionality of optical sensors 14 integrated into AR headset 40 may be similar to that of optical sensors 14 described elsewhere herein. Specifically, such optical sensors 14 may collect 3D optical data, except such 3D optical data may be from the perspective of practitioner 25, which may include the locations and/or orientations of the hands 25A, fingers and/or head 25B of practitioner 25. The 3D optical data may be transformed to the world coordinate frame described above in order to locate and orient the data within OR 36.

IDU display device 16 integrated into AR headset 40 may provide similar functionality to IDU display devices 16 described elsewhere herein. However, IDU display devices 16 integrated into AR headset 40 may project IDU images 18 directly into the eyes of practitioner 25. Such IDU images 18 may, but need not necessarily, comprise three-dimensional images. Because IDU display devices 16 integrated into AR headset 40 project IDU images 18 directly into the eyes of practitioner 25, the corresponding IDU images 18 may appear wherever practitioner 25 is looking and/or adjacent to that location. Similarly, because IDU display devices 16 integrated into AR headset 40 project images directly into the eyes of practitioner 25, workspaces 15, 3D control menus 17 and corresponding menu items 19 may be located wherever practitioner 25 is looking. In some embodiments, one or more 3D control menus 17 may remain fixed in arbitrary positions, either in 3D space or in practitioner's field of view, regardless of where practitioner 25 is looking. For example, a 3D control menu 17 may remain fixed in a corner of the IDU image 18 projected into the eyes of practitioner 25. Practitioner 25 may reposition these 3D control menus 17 as desired. In the particular case of the illustrated example embodiment of system 210 shown in FIG. 1C, AR headset 40 is shown as creating a 3D control menu 17A and IDU image 18A in workspace 15A for controlling surgical light 12A, a 3D control menu 17C and IDU image 18C in workspace 15C for controlling operating table 12C and a 3D control menu 17D and IDU image 18D is workspace 15D for controlling medical image display 12D. In other embodiments, system 210 can create additional or alternative 3D control menus 17 and IDU images 18 in workspaces 15 for controlling additional or alternative medical equipment 12. In some embodiments as is the case in FIG. 1C, 3D control menus 17 and IDU images 18 are created in space. In some embodiments, 3D control menus 17 and IDU images 18 may be projected onto suitable surfaces within OR 36. Techniques for interacting with 3D control menus 17 which are created by AR headset 40 may be similar to interacting with projected 3D control menus 17 described elsewhere herein.

In the illustrated embodiment, system 210 is shown as comprising one or more optional additional 3D optical sensors 14 located external to AR headset 40. Such additional 3D optical sensors 14 can be used to locate practitioner 25 within OR 36 and/or the head 25B of practitioner 25 in OR 36. Such optional additional optical sensors 14 can also be used to locate and/or identify medical equipment 12 in OR 36, to track humans in OR 36 or to otherwise construct a 3D model of OR 36 or a relevant portion of OR 36, as discussed in more detail below.

In some embodiments, AR headset 40 alone or in combination with additional optical sensor 14 detects the location and/or orientation of the head 25B of practitioner 25 and system controller 30 may determine a particular 3D control menu 17 to display to practitioner 25 based on the head 25B of practitioner 25 being oriented toward a particular component of medical equipment 12. For example, if system controller 30 determines (based on information from AR headset 40 and/or additional optical sensor 14) that the head 25B of practitioner 25 is oriented toward medical image display 12D, then controller 30 may elect to display 3D control menu 17D (which may be specific to controlling medical image display 12D) and a corresponding IDU image 18D into a suitable workspace 15D, but if system controller 30 determines (based on information from AR headset 40 and/or additional optical sensor 14) that the head 25B of practitioner 25 is oriented toward light 12A, then controller 30 may elect to display 3D control menu 17A (which may be specific to controlling light 12A) and a corresponding IDU image 18A into a suitable workspace 15A. In some embodiments, a toggle may be provided for each 3D control menu 17 and IDU image 18, so that practitioner 25 may elect whether or not to have such 3D control menu and IDU image 18 presented. In some embodiments, system controller 30 may elect not to display any 3D control menu 17 (based on information from AR headset 40 and/or additional optical sensor 14). For example, system controller 30 may elect not to display any 3D control menu 17 when the head 25B of practitioner 25 is oriented toward a body part being operated on.

In some embodiments, AR headset 40 may additionally or alternatively comprise suitable hardware and software to implement gaze tracking and such gaze tracking techniques may also be used in electing to display particular 3D control menus and IDU images 18 based on gaze direction toward a particular component of medical equipment or toward a body part that is being operated on. One, among many, suitable gaze tracking techniques is described, for example, in PCT/CA2008/000987, which is hereby incorporated herein by reference. Gaze tracking may permit more granular control than would be possible by just tracking head location and orientation. Implementation of eye tracking may additionally or alternatively allow estimate of gaze depth. Gaze depth estimation can be used for knowing when practitioner is looking at 3D control menu 17 located in a workspace 15 between practitioner 25 and a component of medical equipment 12 or to the medical equipment 12 itself.

In some embodiments, AR headset 40 may additionally or alternatively comprise suitable hardware and/or software to implement orientation control. For example, AR headset 40 may comprise one or more sensors for sensing and/or interpreting the movement or orientation of hand(s) 25A of practitioner 25. A particular movement/orientation may correspond to the selection of a particular item 19 on 3D control menu 17, or may manipulate (e.g. rotate or translate) an IDU image 18. The orientation sensors may additionally or alternatively be provided on a handheld device or gloves worn by practitioner 25. In some embodiments, practitioner 25 may move between selections of items 19 on 3D control menu 17 by rotating their hand(s) 25A in a suitable direction. Such rotation may avoid the need for practitioner 25 to move their hand(s) 25A between volumetric spatial regions of 3D control menu 17. As a consequence of controlling the menu, orientation control may be used to control any of the mentioned equipment in the OR. In specific cases where the controlled device is an imaging workstation, this orientation control modality can be used to directly manipulate the displayed image (eg. 3D Rotation, transformation, etc. of the image).

3D Optical Sensors

By means of 3D optical sensing via one or more 3D optical sensors 14, the systems described herein determine the real-time position and orientation of objects of interest within the fields of view of sensors 14. Primarily, the practitioner's hand 25A (for menu interactions) and obstructions within the workspace 15 (for menu configuration) are of interest. By increasing the field of view of sensor 14 or providing additional 3D optical sensor(s) 14, the torso and/or head 25B of practitioner 25 may also be tracked to determine the location of practitioner 25 and the practitioner's head location and/or orientation.

System Controller

System controller 30 comprises one or more processing units which connect to 3D optical sensors 14, control modules 32 and IDU display device 16. System controller 30 processes 3D data from 3D optical sensors 14 and determines the location and orientation of objects within workspace 15, which may include the hand(s) 25A, torso and/or head 25B of practitioner 25. Based on this 3D optical information, system controller 30 may send commands (corresponding to the practitioner's interactions with 3D control menu 17) to medical equipment 12 via appropriate control module(s) 32.

Control Modules

Control modules 32 interface with medical equipment 12 to pass on commands from system controller 30. Specifically, control modules 32 may receive electronic commands from system controller 30 via any suitable wired or wireless communication protocol, translate such commands into specific control commands corresponding to medical equipment 12 and communicate these specific control commands to medical equipment 12. That is, control modules 32 may be retrofitted to legacy medical equipment 12 (in addition or in the alternative to the existing control/communication interface(s) of the legacy medical equipment 12). In some embodiments, some portions or all of control modules 32 may be implemented by system controller 30. In some embodiments, some portions of, or all of, control modules 32 may be implemented within medical equipment 12. Where all of a control module 32 is implemented within a medical device, system controller 30 can interface natively with such medical equipment 12.

A non-limiting example of a control module 32 is a USB dongle, which may plug into a radiology image workstation 12D. The dongle may receive commands wirelessly from system controller 30 and may translate these commands into mouse and keyboard commands, which are sent to radiology image workstation 12D to manipulate images displayed thereon.

In some embodiments, control modules 32 may comprise displays which may be located relatively proximate to their respective components of medical equipment 12. Such displays may be part of the corresponding medical equipment 12 or may be retrofitted onto legacy medical equipment 12. In such embodiments, the displays of control modules 32 can be used as IDU display devices 16 for displaying IDU images 18 back to practitioner 25, so that the practitioner 25 can relatively easily control a component of medical equipment 12 when looking at the medical equipment 12 (or more precisely at the display of the control module 32 corresponding to the medical equipment 12).

A number of exemplary and non-limiting types of medical equipment 12 and interfacing control modules 32 include the following.

Medical imaging devices 12, such as the C-Arm and/or other intra-op imaging devices General C-Arm positioning and activation
  Medical imaging devices 12 (such as the C-Arm and/or other medical imaging devices 12) may comprise their own control panel 13 (e.g. C-Arm control panel 13B and bed control panel 13C as shown in FIG. 1B) that may be connected to the device or hanging down from a ceiling mount and moveable within the operating room. A control module 32 can be interfaced with the control panels 13 of these imaging devices 12 to enable the systems described herein to control the position of the imaging device 12 and to activate the device 12 for procuring images of patient 24 during surgery.
Robotic C-Arm manipulation—Robotic C-Arms used to support medical imaging equipment are provided by a number of different medical device manufacturers, including by way of non-limiting example, the Artis Zeego™ by Siemens Healthcare, the Veradius Neo™ by Philips and/or the like.
  C-Arm mounted imaging devices 12 may provide extended range and positioning capabilities and can also be controlled in the same or similar manner by the systems described herein.
  Many models allow for particular configurations to be set up prior to a surgery—allowing various types of image procurement of patient anatomy information.
  The systems described herein could enable practitioner 25 to select from these configurations using a simple menu interface.
  C-Arms and the imaging systems and/or other medical equipment mounted thereon may be permanent fixtures in an OR 36 or may be mobile, such that the C-Arm can be wheeled into (or otherwise moved into) OR 36.
Image Navigation Devices 12
PACS workstations—pre-op or inter-op, ultrasound workstations, biopsy positioning
  Such image navigation workstations 12 are usually controlled by either a standard or specialized keyboard. For these situations the corresponding control module 32 may take the form of a USB dongle which may control the image navigation workstations 12 via the USB HID protocol. Non-limiting examples of commands that the systems described herein could effect through such control modules 32 include: image manipulations (including brightness, contrast, pan, zoom, scroll, rotation and other angular orientations in the 2D and 3D space and/or the like), adjustments of viewing configurations, image-based measurements (geometric and spatial), user-drawn markings (for communication and referencing), and selection of various image-sets.
Operating Room (OR) Controls 12
Monitor controls
  Some ORs have a composite screen which can display outputs from several devices on a single screen in a customizable configuration. In other ORs several hanging monitors can be switched to display output from various devices. The systems described herein can control the display configuration through a control module 32 interfaced with the control panels 13 for such displays. Through this control module 32 the systems described herein can facilitate presentation of desired data on the monitor of choice.
Room lighting and/or surgical lights
  During certain procedures, it's common for practitioner 25 to adjust the lighting in the room several times. A control module 32 can interface with the lighting control panel 13 to enable practitioner 25 to use the systems described herein to switch and control the intensity of lights in the OR.
Electronic patient medical data access
  Sometimes, touch screen or computer panels inside the OR allow quick access to patient medical data. In some cases, it may be useful to allow practitioner 25 to have sterile control of such a panel to ascertain certain facts about patient 24. The systems described herein could allow practitioner 25 to use the 3D control menu to navigate sections of the patient data and scroll through as desired. Such patient data could be displayed on a physical screen or a virtual screen as a projector or VR glasses.
Replacement of Input Device(s) for Various Medical Equipment
A variety of existing medical equipment (including, for example) medical image displays and/or medical imaging equipment is not currently usable by the practitioner 25 in the OR 36, because such equipment comprises hand-operated input devices (e.g. a keyboard, a touch screen and/or a mouse).
  Medical equipment 12 controllable by the systems described herein may include such medical equipment. The hand-operated input devices of such medical equipment may be bypassed using 3D control menus 17 and control modules 32 which generate commands (based on practitioner interaction with 3D control menus 17) which replace the commands of the hand-operated input devices. For example, practitioner 25 may control any means of a floor- or ceiling-mounted articulated arm, including those of surgical robots, using the systems described herein.
Interaction Display Unit (IDU)
  The 3D control menu 17 that practitioner 25 interacts with is virtual/invisible. The purpose of the IDU (and specifically the IDU display device 16 and its corresponding IDU image 18) is to visually inform practitioner 25 of the location and configuration of the 3D control menu 17, as well as to provide feedback regarding the interaction of practitioner 25 with the 3D control menu 17. This allows practitioner 25 to focus on the IDU, and not their hand(s) 25A. By way of non-limiting example, IDU image 18 may provide indicia indicative of the selection of a particular menu item 19 (e.g. the menu item may change color when the hand 25A of practitioner 25 hovers over the particular menu item). As discussed above, IDU image 18 may also comprise medical image data. IDU display device 16 and corresponding IDU images 18 may take various forms as discussed herein. Details of a number of embodiments are described further below.
  Surface Projection
  One modality of the IDU comprises an IDU display device 16 which projects an IDU image 18 (comprising icons representing menu interface items 19 of 3D control menu 17) on a surface within workspace 15. This is the case, for example, with IDU display device 16 and IDU image 18 of system 10 shown in FIG. 1A and IDU display device 16A and IDU image 18A of system 110 shown in FIG. 1B. The icons of projected IDU image 18 may indicate the locations of the volumetric spatial regions corresponding to menu interface items 19 of 3D control menu 17 and associated with corresponding controls. When practitioner 25 moves their hand 25A into the volumetric region corresponding to a particular menu item 19, the corresponding icon may change color or otherwise change to provide some visual feedback indicator to practitioner 25 of the location of his or her hand 25A within the volumetric spatial region. A finger-tap gesture over, or otherwise proximate to, a given icon can then be detected to actuate controls associated with the menu item 19. Other similar gestures may be used for other common controls (activation gesture, pause gesture, etc.).

In the illustrated embodiments of FIGS. 1A and 1B, IDU display device 16 projects onto the surface 20 of an operating table 22 on which a patient 24 is located. This is not necessary. A projection type IDU display device 16 may additionally or alternatively project IDU image 18 on any given surface in OR 36. Such a surface could be a flat panel next to one or more components of the equipment 12 under control. Such a surface may be covered with a drape or sterile covers during the surgery (i.e. projecting onto those drape regions). Where IDU display device 16 projects IDU image 18 onto an irregular surface (e.g. the surface 20 of an operating table 22), the projected IDU image 18 may be augmented using a method for projection correction (described elsewhere herein), such that practitioner 25 sees an undistorted IDU image 18.

In some embodiments, the color and/or pattern of IDU image 18 may be adjusted to enhance contrast from the surface onto which IDU image 18 is projected for better visibility. For example, if the surface has blood splatter on it, an alternating pattern or the like can be used in IDU image 18 to enhance the contrast over the non-uniformly-colored surface.

In some embodiments, the IDU is implemented using haptic feedback, for example by way of ultrasonic waves. In such embodiments, information from the IDU is relayed to practitioner 25 via their sense of touch, rather than their sense of vision.

Hand Projection:

Another modality of the IDU comprises an IDU display device 16 which projects an IDU image 18 onto the hand 25A of practitioner 25 within workspace 15. This embodiment may, but does not typically, project a representation of the 3D control menu 17 onto a surface. Instead, this embodiment may involve projection of feedback only onto hand 25A of practitioner 25 when it moves through the volumetric spatial regions associated with the various menu items 19. When practitioner 25 moves their hand 25A into a given menu region, an icon representing the corresponding control may be projected onto the hand 25A of the practitioner 25. The projected icon may be augmented according to the curvature of hand 25A to appear undistorted to practitioner 25. By sweeping their hand 25A laterally in front of them, practitioner 25 can move between volumetric spatial regions of the 3D control menu 17 and actuate the corresponding menu items 19 using suitable gestures (e.g. point, finger-tap and/or the like).

Figure 2:
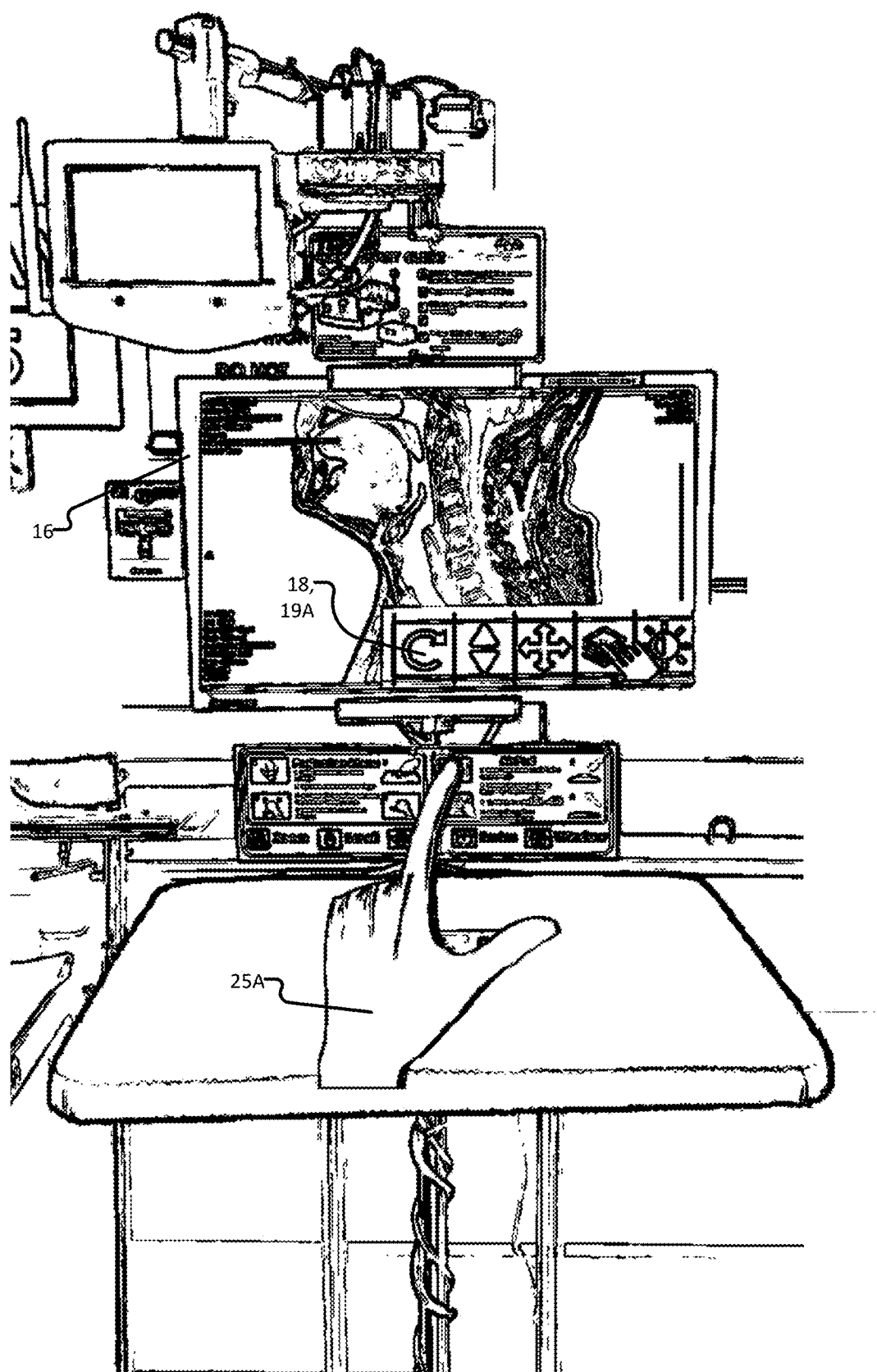
FIG. 2 schematically depicts an Interaction Display Unit (IDU) image overlaid on a physical display, according to one embodiment of the invention.

Physical External Display:

Another modality of the IDU comprises an IDU physical display 16 which displays an IDU image 18 comprising a 2D representation of the 3D control menu 17. The display that displays IDU image 18 may comprise a dedicated display or the 2D representation of the 3D control menu 17 may be overlaid as a "GUI overlay" on some other display (such as a display for displaying medical images), which display itself might be medical equipment 12 controlled by the systems described herein. The GUI overlay (for example, IDU image 18 as shown in FIG. 2) may allow for markers to be drawn or placed over a medical image in locations selected by practitioner 25. A depiction of the hand 25A of practitioner 25 may also be displayed to inform practitioner 25 of the proximity and location of their hand 25A relative to the volumetric spatial regions in the 3D control menu 17. The 2D representation of IDU image 18 can display special icons or animations to feedback information to practitioner 25 about hand motions (e.g. gestures) performed in real-time.

IDU physical display 16B and corresponding IDU image 18B of system 110 depicted in FIG. 1B represents an example of an embodiment where IDU image 18B comprises a GUI overlay on a medical image display 12D, which display 12D is itself medical equipment 12D controlled by the system 110. In embodiments where the GUI overlay corresponding to IDU image 18 can be overlaid on the same display 12D where medical images are displayed in the OR, practitioner 25 will have the choice to look down at the projected 3D control menu for interactions or to use the GUI overlay corresponding to IDU image 18 on the medical image display to do the same. The IDU physical display 16 may display an IDU image 18 comprising a representation 18A of hand 25A of practitioner 25 (or any other object being used for interaction—e.g. a scalpel) and its relative position to the volumetric menu regions (as shown in FIG. 2).

In such embodiments, practitioner 25 need not to look down to see the projected 3D control menu 17 while they are trying to focus on controlling OR equipment (e.g. navigating radiology images on a medical image display 12D or rotating the C-arm 12B). When practitioner 25 moves their hand 25A within workspace 15, the GUI overlay would display the relative position of hand representation 18A within IDU image 18 in real-time. The same or similar visual feedback techniques used for the projected IDU image 18 can be employed for the physical display IDU image 18. For example, highlighting of a particular icon upon selection could also be reflected on the IDU image 18 shown by the physical display 16. It should be noted that in this case IDU image 18 and the projected 3D control menu 17 work independent of each other. The physically displayed IDU image 18 does not need projected 3D control menu 17 to function and vice versa.

As mentioned above, it is not necessary that the physical IDU display 16 be a display that is used for other purposes or that the IDU display 16 be a component of medical equipment 12 controlled by the systems described herein. Instead, in some embodiments, IDU display 16 may comprise a dedicated display for displaying IDU image 18. This is the case, for example, with dedicated IDU display 16C and corresponding IDU image 18C of system 110 shown in FIG. 1B. Such a dedicated IDU display 16 may be positioned in any convenient location in OR 36 for this purpose (ideally adjacent to medical equipment 12 under the control of the systems described herein for ease of control of such equipment 12).

As discussed above, control modules 32 may comprise displays which may be located relatively proximate to their respective components of medical equipment 12 and such displays can be used as physical IDU displays 16 for displaying IDU images 18, either as dedicated IDU displays 16 or as an IDU image 18 overlaid on a display 16 that also displays other information (e.g. medical image data).

Augmented Reality IDU Display

Figure 3:
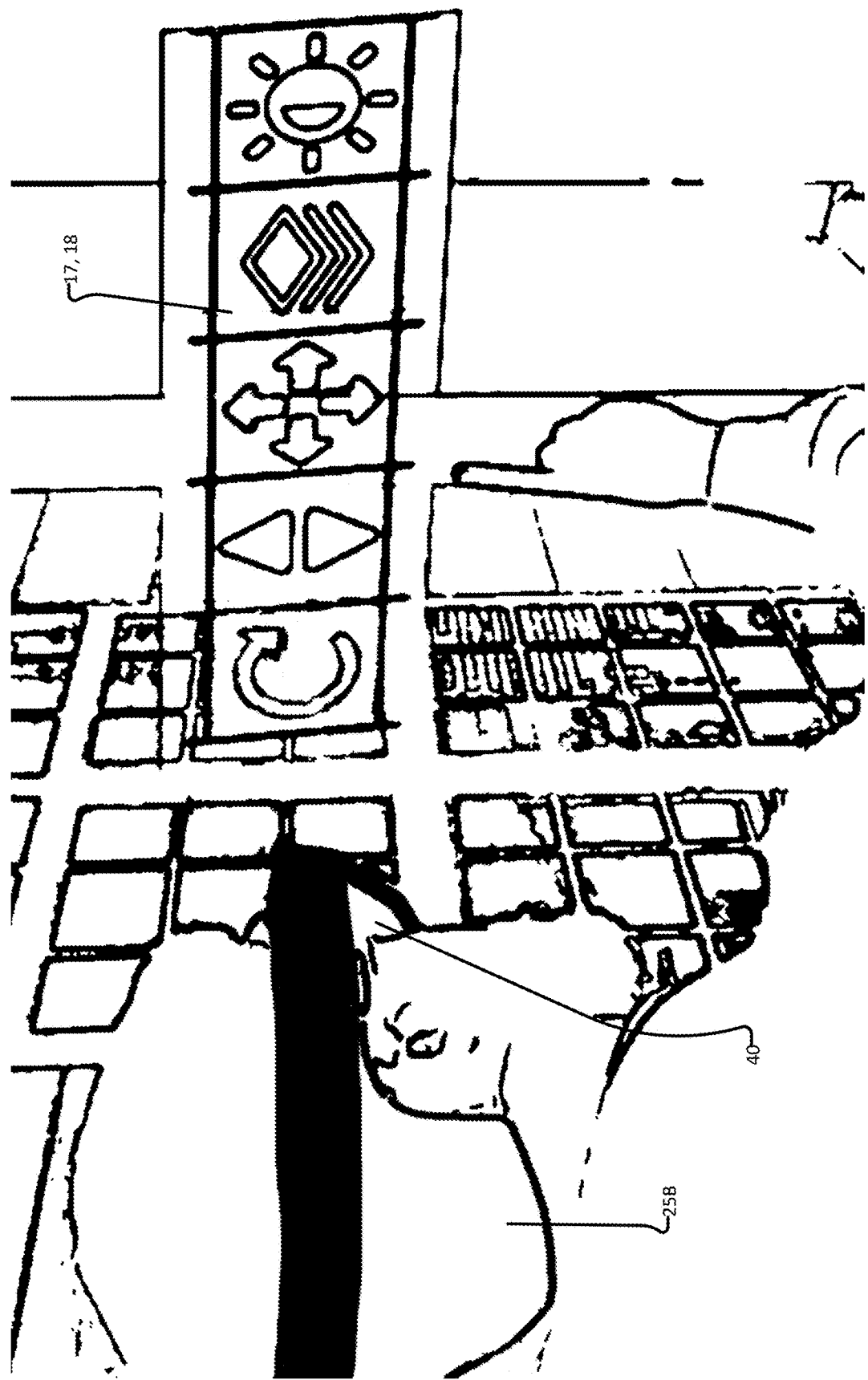
FIG. 3 schematically depicts a practitioner wearing an AR headset, according to one embodiment of the invention.

FIG. 3 schematically depicts a practitioner 25 wearing AR headset 40 and a 3D control menu 17 and corresponding IDU image 18 according to an example embodiment. As discussed above, where practitioner 25 wears an AR headset 40, IDU display device 16 is integrated into AR headset 40 and projects AR image 18 directly into the eyes of practitioner 25. As such, IDU images 18 can be located wherever practitioner 25 is looking as shown in FIG. 1C. In some embodiments, two separate IDU images may be projected into the eyes of practitioner 25, so that practitioner 25 sees 3D IDU images 18. As also discussed above, the head orientation and/or gaze orientation of practitioner 25 can be used to select between 3D control menus 17 and corresponding IDU images 18 to display (or whether to display such menus/images at all). In some embodiments, practitioner 25 can "pin" 3D control menus 17 and corresponding IDU images 18 to particular locations, so that such menus/images only appear when the head orientation and/or gaze orientation of practitioner 25 is directed to that location.

A system like system 210 which makes use of an AR headset 40 may be advantageous in some circumstances, because suitable 3D control menus 17 and corresponding IDU images 18 can be located in the direction of corresponding medical equipment 12 which is intuitive and easy for practitioners to use. However, physical 3D control menus 17 and corresponding IDU images 18 can be advantageous where multiple practitioners 25 are working cooperatively. If a projected or physical form of 3D control menu 17 and corresponding IDU image 18 are used, it is easier to communicate and collaborate, because one practitioner 25 can see what the other is doing without needing any extra equipment.

Projection Correction

As discussed above, in some embodiments, IDU display device 16 projects an image corresponding to a 3D control menu 17 and/or a corresponding IDU image 18 onto a surface, such as, for example, the surface 20 of an operating table 22 on which a patient 24 may be located. A typical operating table 22 in a busy OR 36 is hardly an ideal environment to act as a projection surface—due to geometrical irregularities and deformations (e.g. drape wrinkles, the presence of patient 24, the presence of surgical tools, etc.). Such an irregular surface may cause geometric distortions in any image projected thereupon, making the projected image appear warped from the perspective of practitioner 25. Such warping of images corresponding to control menus 17 and/or IDU images 18 can hinder system usage and user clarity. For example, a practitioner 25 may be performing a surgical procedure on a patient's chest area. The upper half of the patient's body may accordingly be surrounded by various surgical tools and devices. In this situation, the system would be most optimally placed such it that can project 3D control menu 17 and/or IDU image 18 over the patient's lower torso/legs. However, whenever projection is done on irregular or curved surfaces, the projected IDU image 18 may be warped and difficult to see and, consequently, the corresponding 3D control menu 17 may be difficult to use.

Aspects of the invention provide methods and systems for homographic correction of such warping of projected images. Using such techniques, 3D control menu 17 and/or IDU image 18 may be pre-adjusted such that projected graphic content (projected adjusted images) appear undistorted from the perspective of practitioner 25. These techniques compensate for deformations and irregularities on the projection surface. While these techniques are applicable to any projection surface, these techniques are described herein for the case where the projection surface is the surface 20 of an operating table 22 on which patient 24 may be located without loss of generality. Similarly, these techniques assume that the projector that is projecting the image is an IDU display device 16 of the type shown in FIG. 1A and at 16A in FIG. 1B, without loss of generality.

When projecting 3D control menu 17 and/or IDU image 18 on an irregular projection surface 20, no matter how the projector (e.g. IDU display device) 16 is positioned and oriented with respect to surface 20, the resulting image will look distorted from the practitioner's point of view, in the absence of pre-adjustment. However, there is one point in space from which the projected image looks perfectly linear and undistorted (i.e. non-warped)—the position of projector 16. To see a non-distorted projection image (of 3D control menu 17 and/or IDU image 18) from an arbitrary viewpoint (which may be considered to be the viewpoint of practitioner 25), the original image may be pre-adjusted to provide an adjusted image and the adjusted image may be projected such that it appears as if it was projected from the arbitrary viewpoint.

Projection surface 20 may be scanned using 3D optical sensor(s) 14 and, based on the 3D data relating to the projection surface 20 obtained from sensors 14, the curvature of projection surface 20 may be characterized. Parts of the original image that align with regions of positive curvature on projection surface 20 may be calibrated to the same degree of distortion caused by equivalent negative curvature, and vice-versa for regions of projection surface 20 exhibiting negative curvature. The resulting adjusted image, when projected onto projection surface 20 appears linear or otherwise non-distorted and non-warped from the perspective of practitioner 25.

The location of practitioner 25 and the point-of-view of practitioner 25 are parameters used to determine how to adjust the original image and to thereby provide the adjusted image. Specifically, a projection from the viewer's perspective may be simulated to determine the adjustments to make to the original image. In some embodiments, information about the location and/or orientation of the head 25B of practitioner 25 may be ascertained by one or more optical sensors 14 described above. In some embodiments, the location of the head 25B of practitioner 25 may be ascertained by one or more optical sensors 14 described above and the orientation of the practitioner's head 25B may be estimated from the location. In some embodiments, one or more additional 3D cameras or orientation sensors (e.g. accelerometers, gyroscopes and/or the like) may be used to determine the location and/or orientation of the practitioner's head 25B. Additional details of techniques for head tracking are described below. It will be appreciated that head location and head orientation are in fact proxies for gaze orientation. In some embodiments, gaze tracking techniques such as those described elsewhere herein may be used to determine the perspective by which practitioner 25 views 3D control menu 17 and/or IDU image 18.

In some embodiments, one or more of 3D optical sensors 14 and/or one or more dedicated 3D optical sensors similar to sensors 14 may be used to track practitioner 25 as he or she moves around OR 36 and/or workspace 15, such that the projected 3D control menu 17 and/or IDU image 18 is always oriented towards practitioner 25. One or more 3D optical sensors 14 might also be used to scan all of, or the relevant portions of, OR 36. A suitable machine vision method (e.g. surface feature localization by surface normal estimation) can then be used to perform a curvature analysis on the scanned OR 36 for determining the best (e.g. flattest) projection surface 20. Following this, an articulated robotic arm 50 might be employed (under the control of system processor 30) to automatically position IDU display projector 16 in a suitable location for projecting on the desired projection surface 20. This process of using articulated robotic arm 50 is described in more detail below.

The location of a practitioner 25 within OR 36 may be identified and/or tracked using point clouds generated by one or more 3D optical sensors 14 suitably mounted within OR 36. Such 3D optical sensors 14 may or may not comprise optical sensors 14 used for detecting interactions with 3D control menus 17. Many such methods can be employed in the medical environment. Such algorithmic processes utilize not only preprocessing techniques (for filtering and smoothing the point cloud), but also techniques for analyzing shapes and curvatures known to be apparent for the human head and upper body.

Methods for projection correction according to particular embodiments, which may be performed by system processor 30, may be broken down into two component methods: surface reconstruction; and projection correction. As a part of surface reconstruction, system processor uses 3D data from 3D optical sensors (e.g. 3D optical sensors 14) or any other suitable sensors to construct a mesh representation of projection surface 20.

Figure 4:
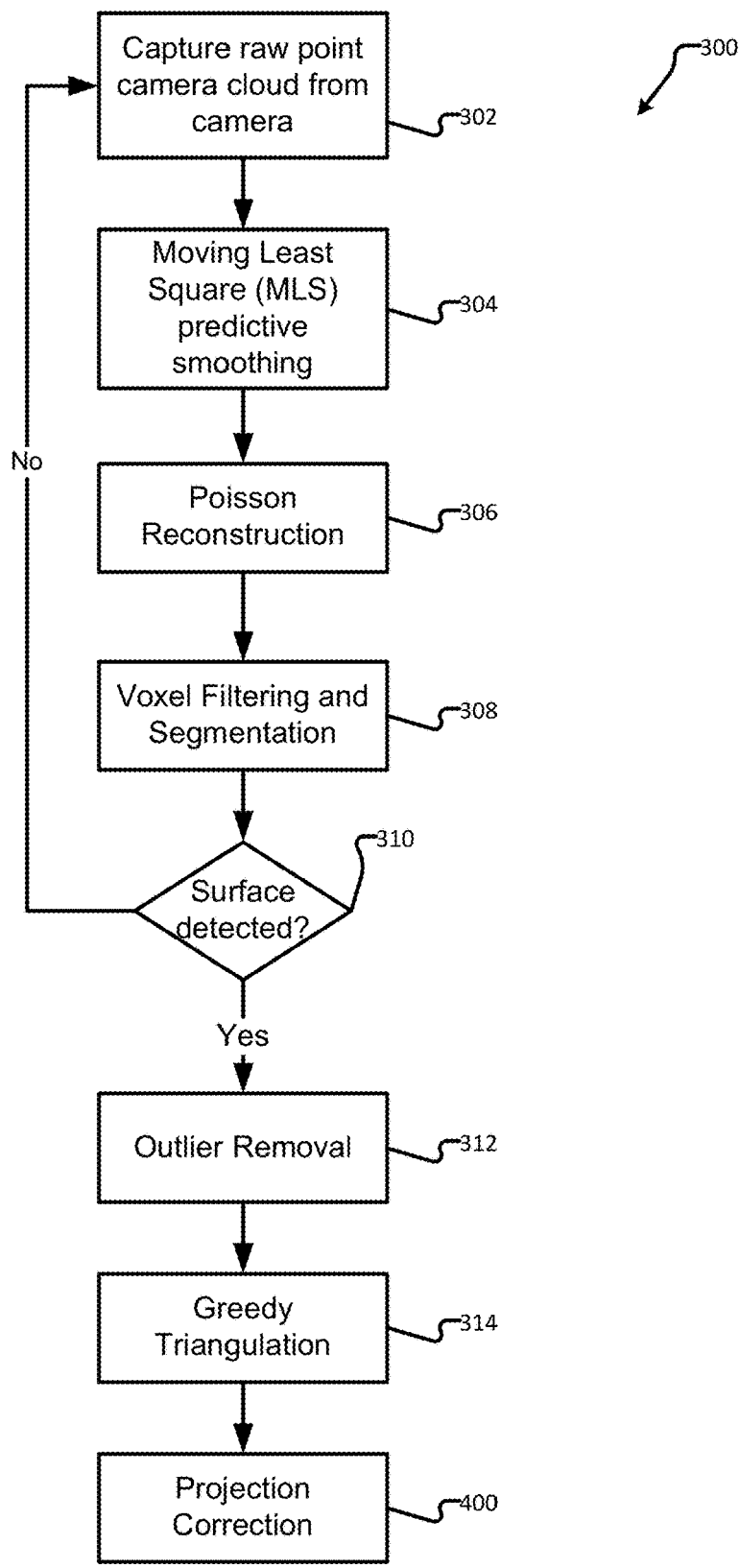
FIG. 4 is a block diagram of a method for surface reconstruction, according to one embodiment of the invention.
Figure 5:
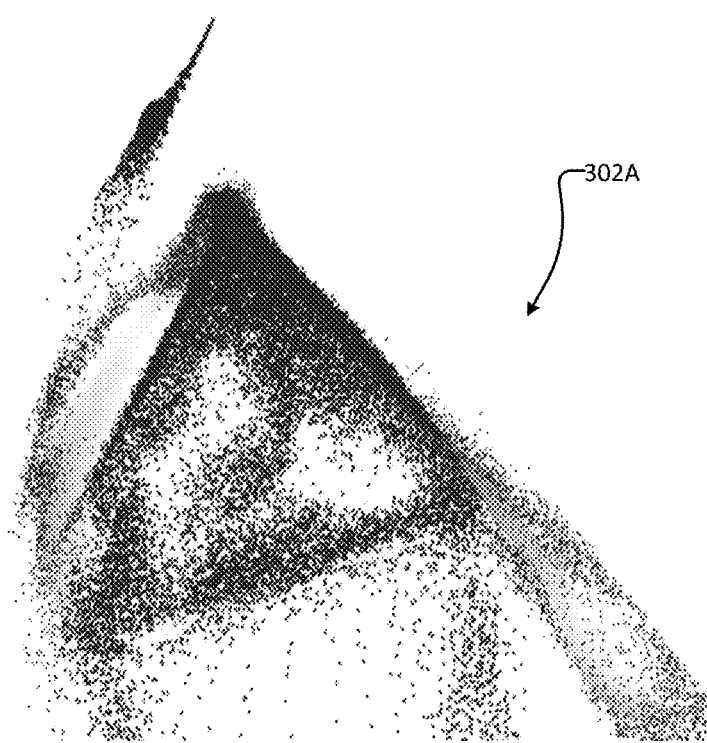
FIG. 5 shows an example representation of a point cloud representing a surface.

FIG. 4 schematically depicts a method 300 for surface reconstruction according to a particular embodiment. Method 300 may be performed by system controller 30. Method 300 begins in block 302 which involves capturing raw 3D data using 3D optical sensors 14 of the type described herein. The output of block 302 comprises a plurality of points in 3D space (referred to as a point cloud or a 3D point cloud) 302A. FIG. 5 shows an example representation of a point cloud 302A in a particular example. As can be observed from FIG. 5 and as is typical in block 302, point cloud 302A does not have uniform point density over the various regions of point cloud 302A. There is a desirability, from the perspective of the illustrated embodiment of surface reconstruction method 300 of FIG. 4, for a relatively more uniform point density in the point cloud.

Method 300 then proceeds to block 304 which comprises smoothing the point cloud 302A obtained in block 302. Although there are many available smoothing techniques (any of which can be used in block 304), block 304 of the currently preferred embodiment uses a moving least squares (MLS) predictive smoothing technique. MLS predictive smoothing is a resampling method that helps to remove and smooth irregularities in point cloud 302A. Such irregularities may be caused, for example, by small distance measurement errors that come from 3D optical sensor(s) 14. The block 304 MLS method comprises attempting to modify the points within 3D point cloud 302A to be more regularly distributed—by filling in points in low density regions with interpolations based on the surrounding points.

Figure 6:
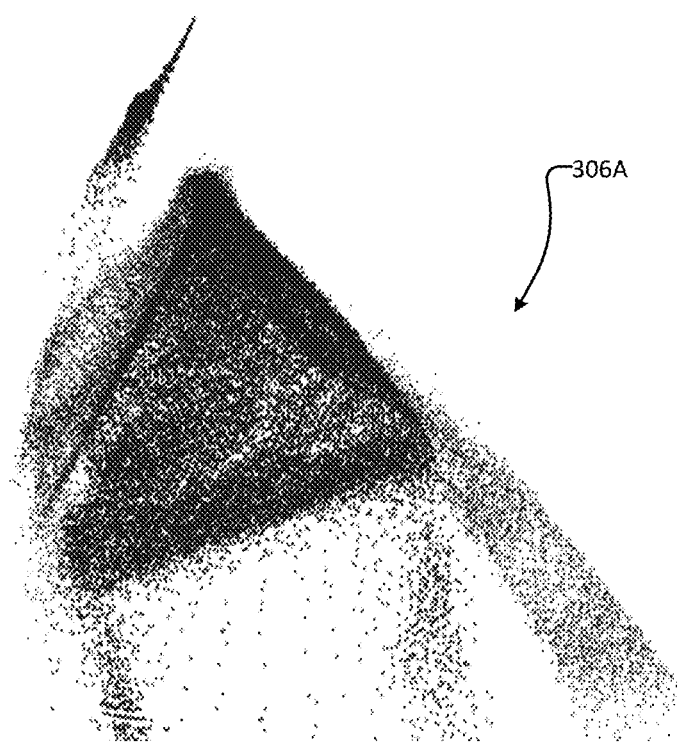
FIG. 6 schematically depicts an example of a point cloud after predictive smoothing and reconstruction are performed on the point cloud shown in FIG. 5.

Method 300 then proceeds to block 306 which comprises reconstruction of the 3D point cloud which may help to fill in holes in some regions which were not captured with desired density by 3D optical sensors 14 in block 302. One particular technique for implementing the block 306 reconstruction procedure is referred to as Poisson reconstruction. Poisson reconstruction helps fill in the holes in certain regions that were not captured with sufficient density by 3D optical sensors 14. This block 306 procedure may comprise analyzing the curvature of surface regions surrounding any holes (absences of points within the point cloud), and then populating each hole with points such that the change in curvature is minimized. FIG. 6 schematically depicts an example of the output 3D point cloud 306A of block 306 after the predictive smoothing of block 304 and the reconstruction of block 306.

Figure 7:
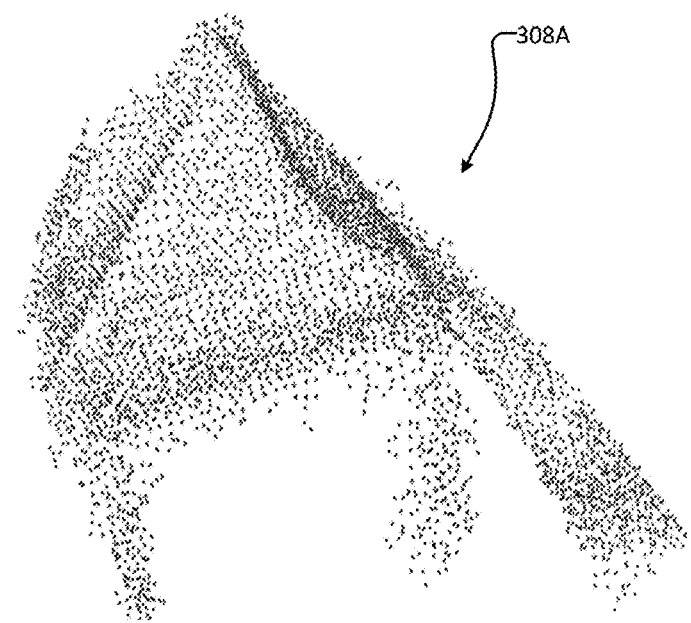
FIG. 7 schematically depicts an example of a point cloud after a voxel filtering process is performed on the point cloud shown in FIG. 6.

Method 300 then proceeds to block 308 which involves voxel filtering and segmentation. Point cloud 306A output from block 306 is dense and is typically populated by more than $3 \times 10^6$ individual points in 3D space. Performing any processing on such a large dataset can be computationally expensive. Thus, from a computational expense perspective, it can be desirable to reduce the size of point cloud 306A, without losing important information about the shape of projection surface 20. This reduction in the size of point cloud 306A may be performed in block 308 by voxel filtering. The block 308 voxel filtering process may involve the use of a voxel grid filter which returns a point cloud with a smaller number of points which optimally represents the input point cloud as a whole. The block 308 voxel grid filter may down-sample the data from point cloud 306A by taking a spatial average, median and/or the like of the points in point cloud 306A. FIG. 7 schematically depicts an example of the output 3D point cloud 308A of block 308 after the block 308 voxel filtering process.

Method 300 then proceeds to block 310 which involves performing an inquiry as to whether a surface can be detected within point cloud 308A output from block 308. Block 310 may comprise evaluating the resultant point cloud to determine whether a surface can be ascertained from the resultant point cloud. If no surface is detected (typically because the main cluster of 3D points in the resultant point cloud is too sparse), then method 300 proceeds along the block 310 NO output back to block 302, where further image data is acquired. On the other hand, if a surface is detected in block 301 then method 300 proceeds along the block 310 YES output to block 312.

Figure 8:
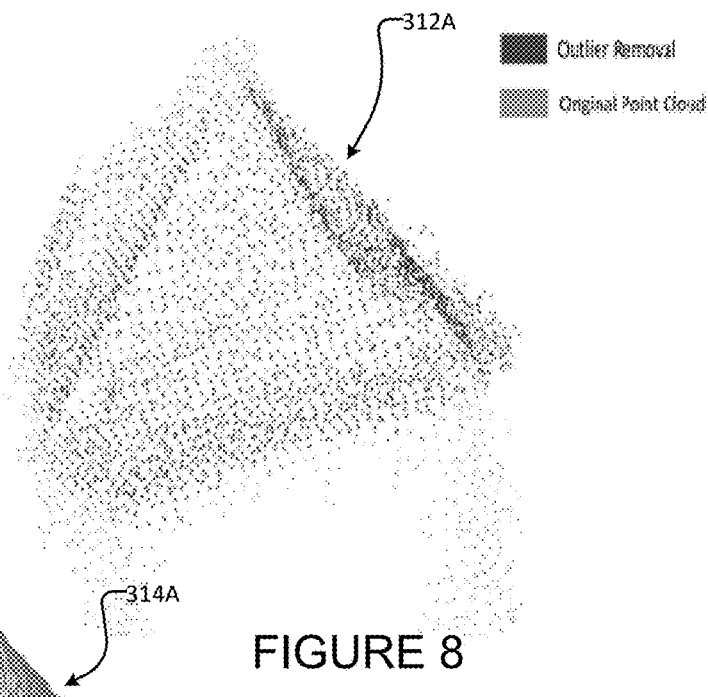
FIG. 8 schematically depicts the point cloud shown in FIG. 7 with outlying points removed.

Block 312 involves removal of outlying points from the point cloud 308A. Due to the nature of some 3D optical sensors (e.g. time of flight sensors), accuracy typically drops along the edges of a captured scene. Therefore, in some embodiments, it can be desirable, for surface estimation, to remove statistically outlying points from point cloud 308A, where such points are sparse and not dense. In some embodiments, the block 312 outlier removal may be based on the computation of the distribution of point-to-neighbor distances in the point cloud 308A received in block 312. For each point, block 312 may comprise computing the mean distance from the given point in the point cloud to its neighbors. Points whose mean distances are outside a configurable (e.g. user configurable) threshold interval may be removed from the point cloud. This block 312 outlier removal process is schematically illustrated in FIG. 8 which depicts both the outlying points removed from the point cloud in block 312 and the remaining point cloud 312A.

Figure 9:
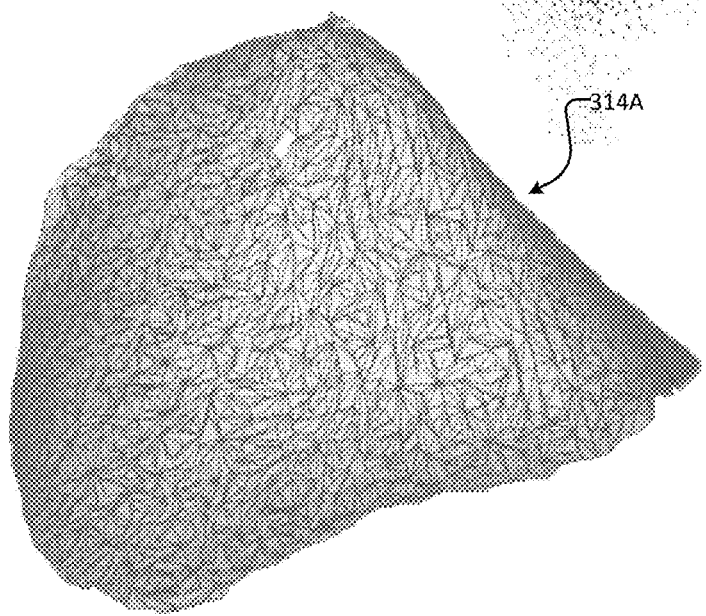
FIG. 9 schematically depicts an example triangulated surface mesh generated from the point cloud shown in FIG. 8.

Method 300 then proceeds to block 314 which involves implementing a triangulation process (e.g. a greedy triangulation process or any other suitable triangulation process) to generate a surface mesh 314A from the block 312 point cloud 312A. The block 312 greedy triangulation process may comprise generating a virtual approximation 314A of the real projection surface 20 by connecting points in the point cloud 312A with triangles. The block 314 greedy triangulation process works by maintaining a list of points from which the mesh can be grown ("fringe" points) and extending the mesh until all possible points are connected, which results in a triangulated surface mesh 314A. FIG. 9 depicts an example triangulated surface mesh 314A output from block 314.

Figure 10:
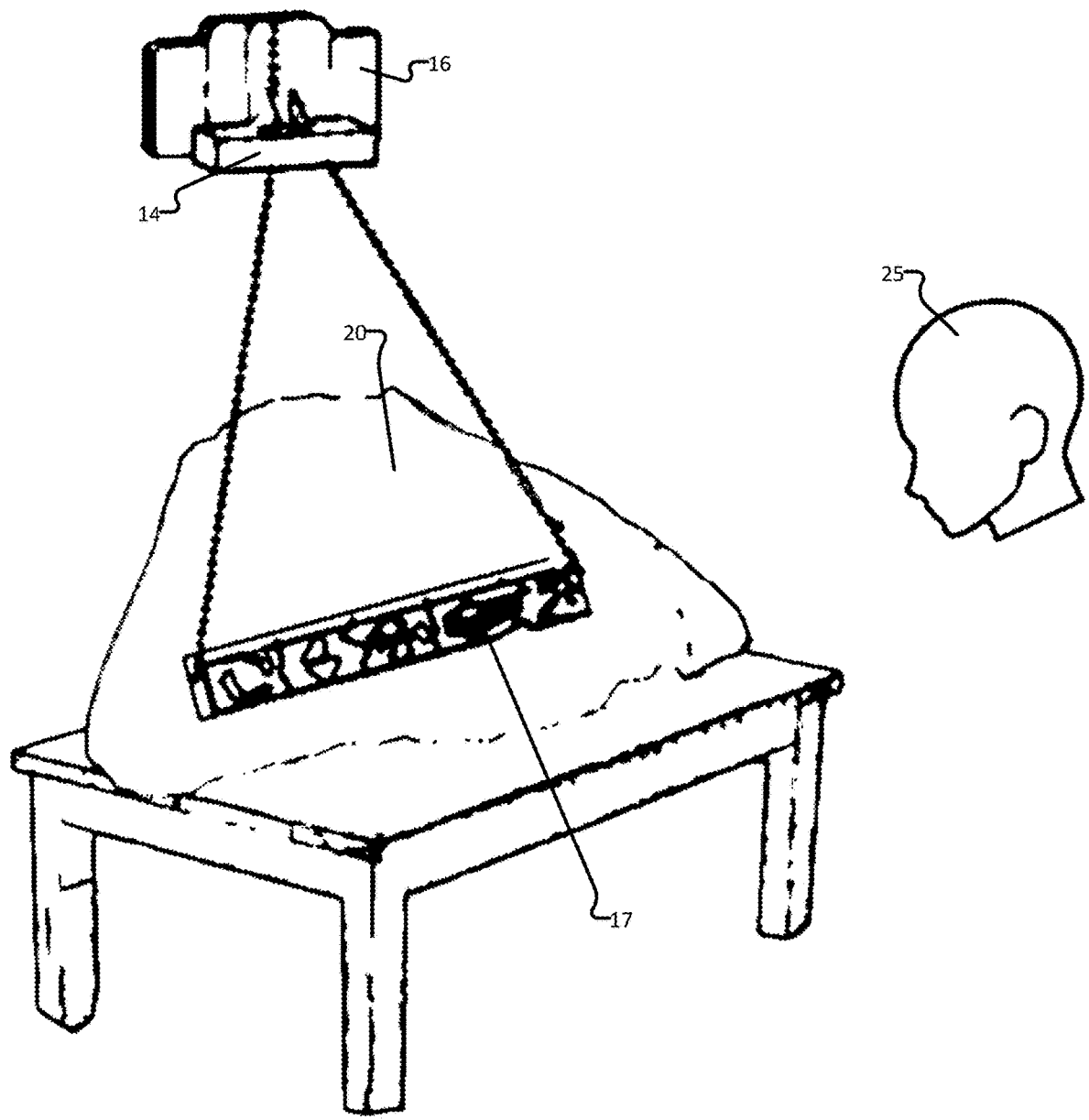
FIG. 10 illustrates a typical set-up of an exemplary system described herein which is used for performing the method shown in FIG. 11.

Once a surface mesh 314A is obtained in block 314, surface reconstruction method 300 is completed and the projection correction method of the illustrated embodiment proceeds to projection correction in block 400. FIG. 10 illustrates a typical set-up of an exemplary system described herein which is useful for the purposes of explaining the block 400 projection correction method. In the FIG. 10 illustrative example a 3D optical sensor 14 and an IDU display device (e.g. projector) 16 are placed above projection surface 20 (e.g. an operating table 22). Projector 16 placed above projection surface 20 projects the 3D control menu 17 and corresponding IDU image 18 of interest, while 3D optical sensor 14 (which is placed close to projector 16) captures projection surface 20 in 3D.

Figure 11:
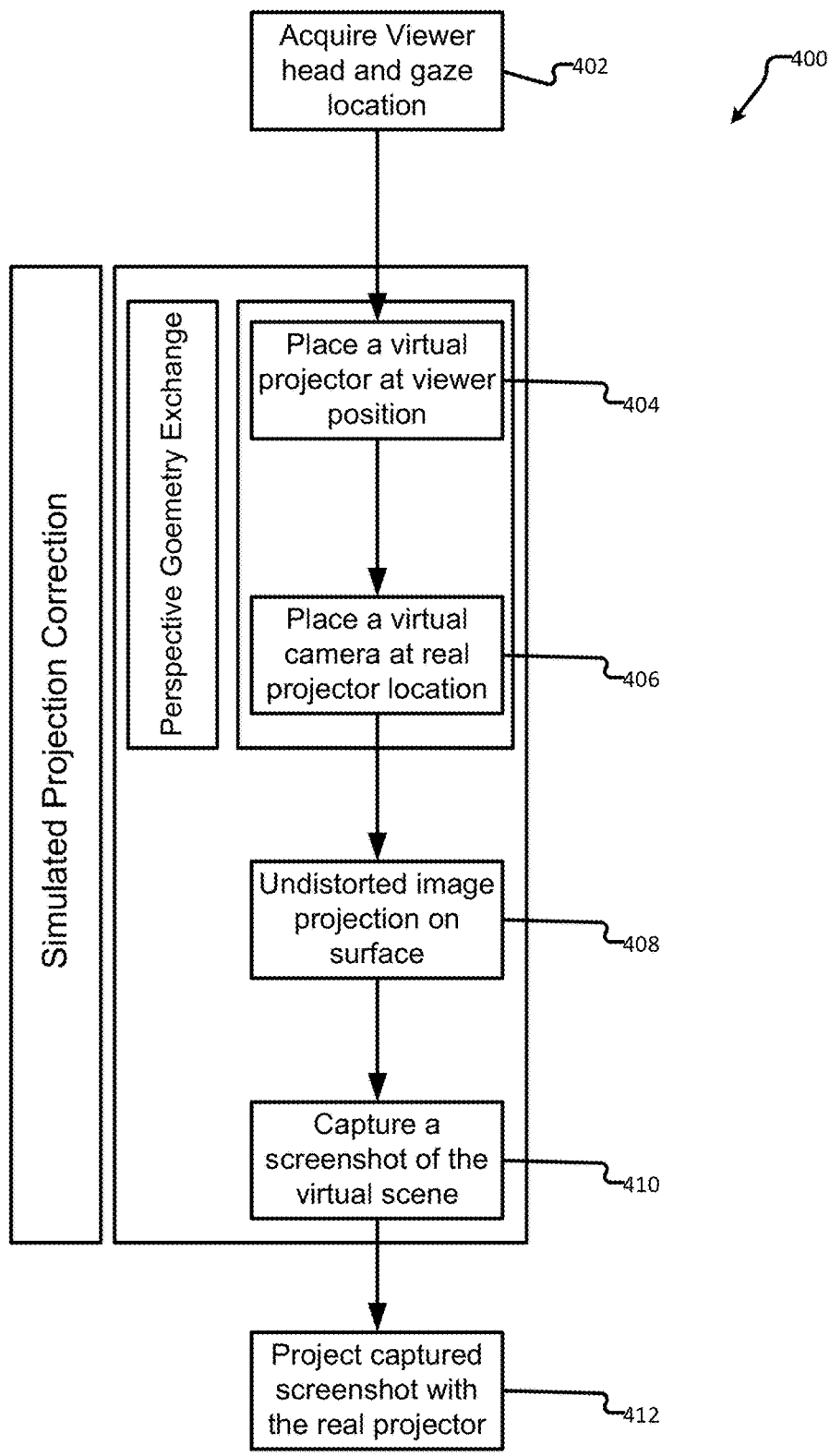
FIG. 11 is a block diagram of a method for implementing projection correction, according to one embodiment of the invention.

FIG. 11 schematically depicts a method 400 for implementing projection correction block 400 according to a particular embodiment. Method 400 begins in block 402 which involves obtaining any available data about the location of the head 25B of practitioner 25 and the gaze direction of practitioner 25. As discussed elsewhere herein, head orientation of practitioner 25 may be used as an estimation of user gaze direction. Head orientation may be detected using a variety of techniques, a number of which are described herein. In some embodiments, head orientation may be estimated based on head location. For example, a vector may be constructed between the estimated head location and the projection surface and it may be assumed that the head orientation of practitioner 25 is directed along this vector. In some embodiments, the vector may be determined by detecting (for example, using one or more optical sensors) Purkinje reflections (i.e. glints) in one or both eyes of practitioner 25.

Blocks 404 and 406 of projection correction method 400 may perform a process referred to as a perspective geometry exchange. Once the practitioner's head location and at least an estimate of the practitioner's head orientation are determined in block 402 and a surface mesh 314A is determined in block 314, a simulation of the real scene maybe created in a graphical engine using a suitable graphics simulation library. Examples of suitable graphics simulation libraries include OpenGL, DirectX, Unreal Engine and/or the like. It is important to appreciate that the steps of block 402 through 410 are performed in a computer-generated virtual scene that aims to approximate the real scene, but is not the same as the real scene. Blocks 402 through 410 involve computational simulations and corresponding steps in such simulations, but no physical projection or sensors are used in the performance of these processing steps.

Surface mesh 314A created in block 314 is placed in the virtual scene. A virtual camera 60 is placed at the same relative position to the simulated mesh as the real world projector is located relative to the real projection surface in the physical scenario. Then a process which may be referred to as a perspective geometry exchange may be performed in the virtual scene. In the perspective geometry exchange, a virtual projector 62 is placed at the viewer's known head location relative to the projection surface in the virtual scene. Simultaneously, a virtual camera 60 is placed at the location of the real projector relative to the projection surface in the virtual scene. Because the practitioner's (viewer's) perspective is replaced with a virtual projector 62, this process is called perspective geometry exchange.

Block 404 involves placing a virtual projector 62 at the location of the practitioner's head in the virtual scene. As discussed above, when a projected image is viewed from the projector location, it will always appear non-distorted, regardless of the shape of the projection surface. The concept behind projection correction method 400 is to move, in simulation, a virtual projector 62 to the same position and orientation as the practitioner's (viewer's) head. When viewed from the practitioner's (viewer's) perspective, this virtual projection will appear undistorted, no matter the shape of the projection surface captured by the 3D optical sensor. It should be noted that the virtual projector's FOV (i.e. throw ratio) and optical characteristics are completely arbitrary and can be set to anything that suits the scene that has been set up.

Figure 12:
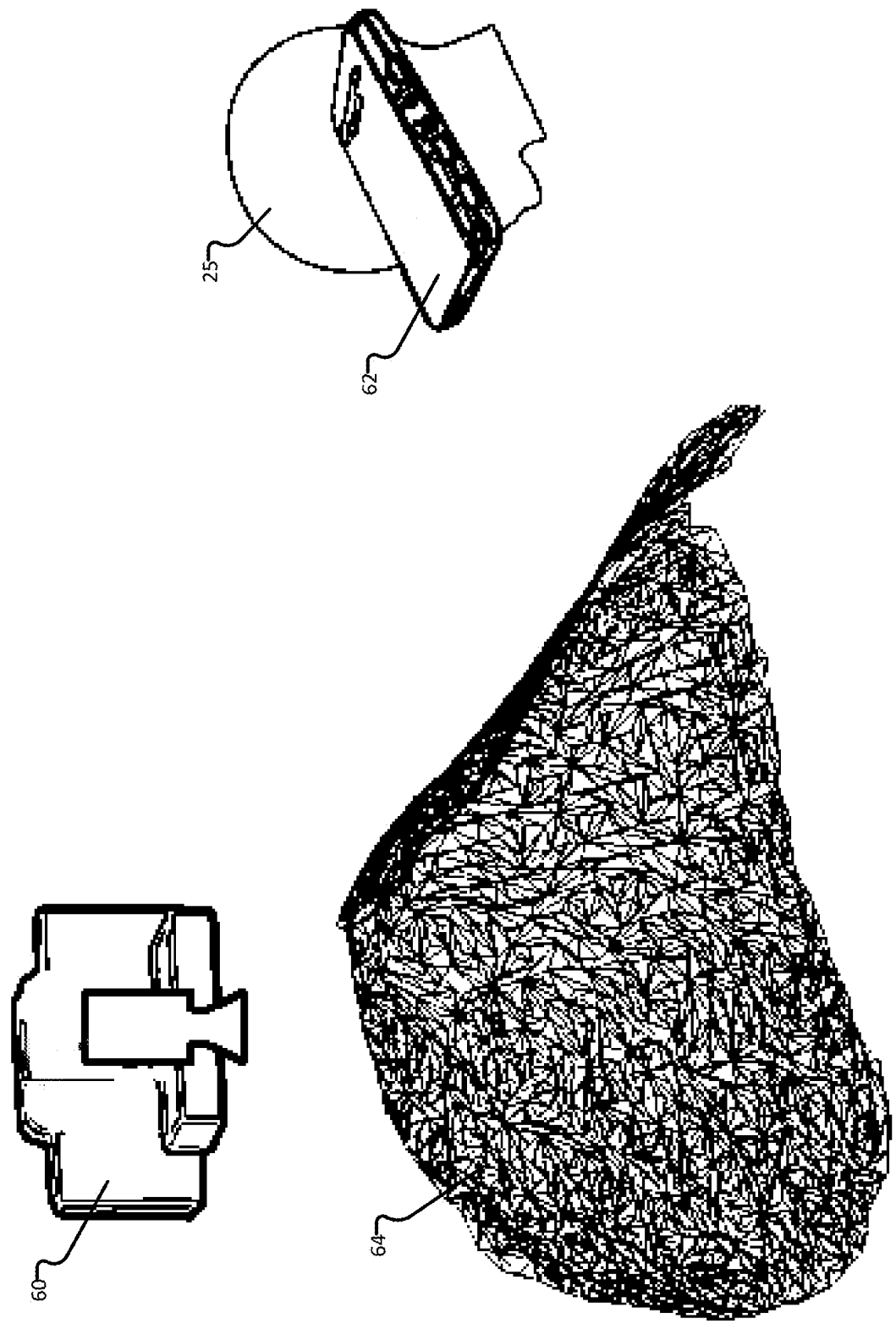
FIGS. 12 and 13 schematically depict a virtual scene used in the method shown in FIG. 11, according to one embodiment of the invention.

Method 400 then proceeds to block 406 which involves placing a virtual camera 60 in the simulated scene at the same location relative to the simulated projection surface as the location of the real projector relative to the real projection surface. Placing the virtual camera 60 in the scene completes the process of perspective geometry exchange. It should be noted that the virtual camera's FOV and optical characteristics (such as throw of camera) are preferably the same as those of the real projector. At the conclusion of block 406, the virtual scene has the configuration shown in FIG. 12.

Figure 13:
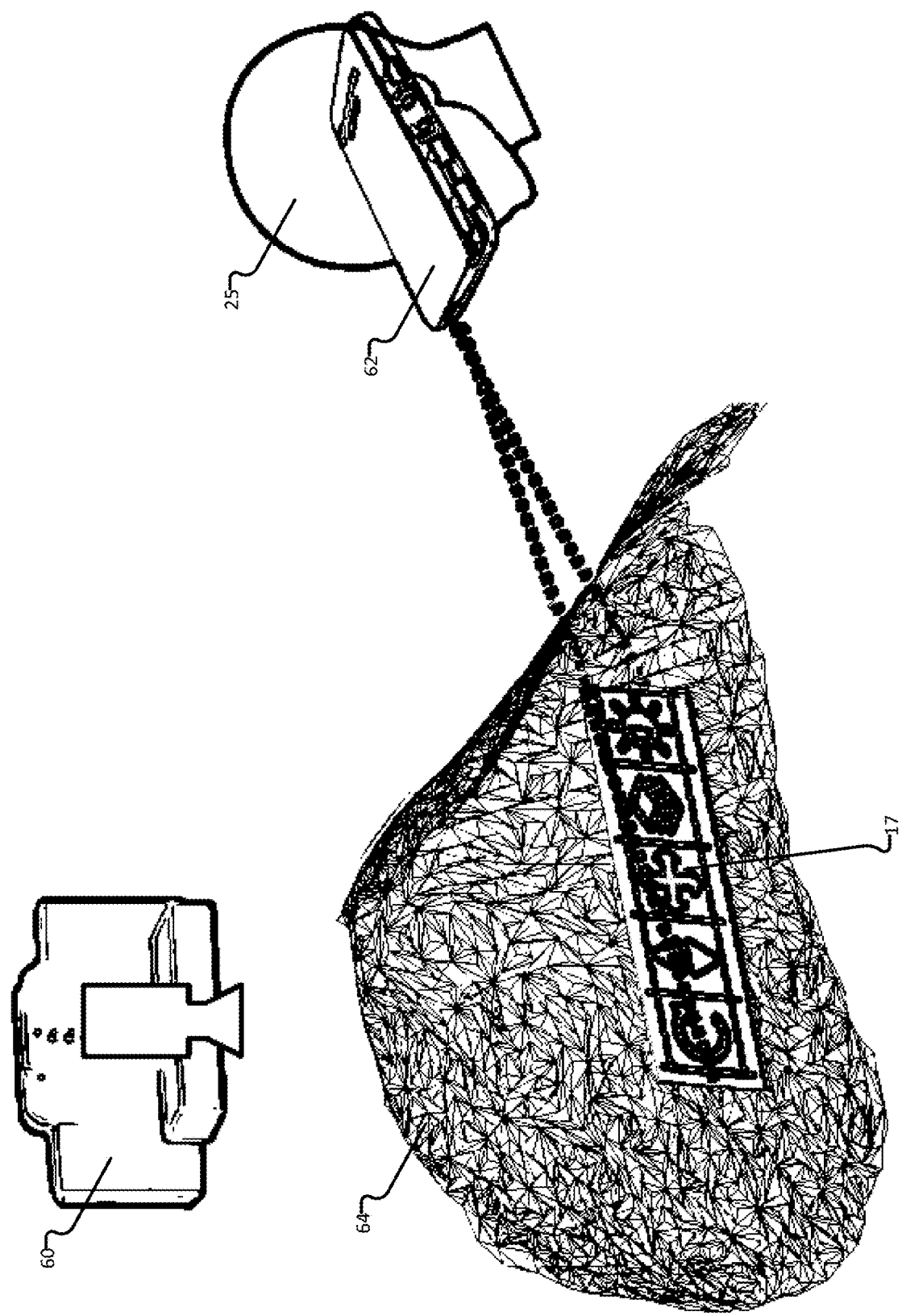

Method 400 then proceeds to block 408, where, using the virtual projector 62 (at the location of the viewer in the simulated scene), the original, undistorted image (e.g. 3D control menu and the corresponding IDU image 18) is projected on the virtual projection surface 64 in the simulated scene as shown in FIG. 13. As the virtual projector 62 is placed at viewer location, from viewer's perspective, this projection would appear undistorted and linear (i.e. non-warped). From any other perspective (including from virtual camera's perspective), the same virtual projection would appear distorted. It should also be noted that FIG. 13 is shown from some arbitrary perspective that does not belong to either the virtual camera 60 or the viewer position. This is done so that reader can better understand the relative positioning of all the components in the simulation.

Figure 14:
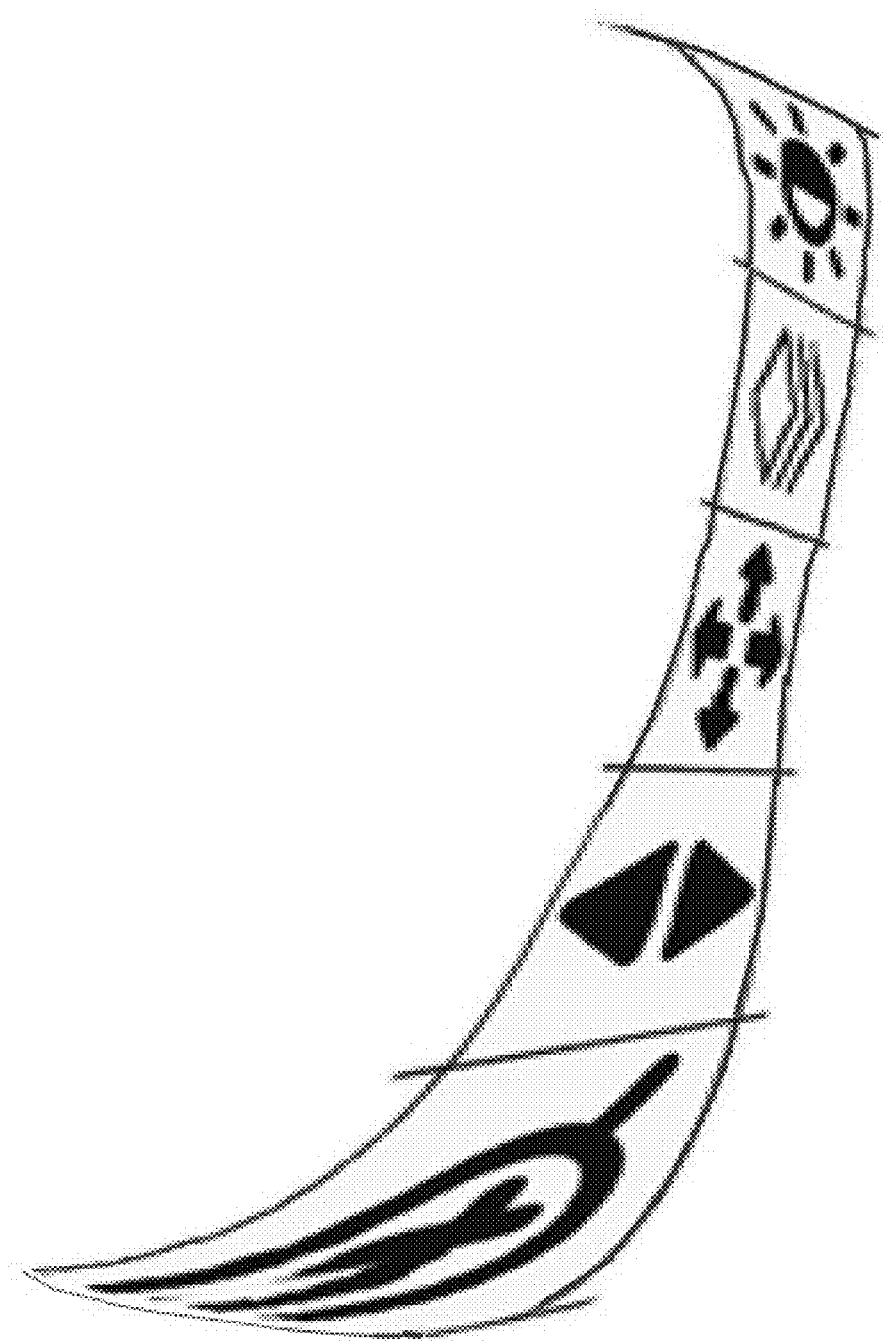
FIG. 14 is a representation of a screenshot showing a distorted image captured by the virtual camera shown in FIGS. 12 and 13.

Method 400 then proceeds to block 410 which involves capturing the virtual scene from the perspective of the virtual camera 60 (and the real projector). The virtual camera's perspective may be captured in block 410 in the form of a screenshot. In this block 410 screenshot (which is taken from the perspective of the virtual camera 60 (and real projector)), the image projected by the virtual projector 60 will look distorted, as explained above. However, as this distorted block 410 image is the same image that is designed (in block 408) to look correct from perspective of the viewer, this same block 410 image, when projected from the real projector, will look undistorted to the viewer. FIG. 14 depicts a representation of a block 410 screenshot showing the distorted image captured by the virtual camera 60. As block 410 is the step where the final input for the pre-adjusted image (for real projection) is captured, the virtual camera's FOV and optical characteristics preferably match the real projector, as discussed above. Block 410 also completes the steps for simulated projection correction, which may be performed in a suitable graphics simulation environment, such as OpenGL, DirectX, Unreal Engine and/or the like. In some embodiments, a graphics simulation environment is not required and the perspective exchange process can be performed analytically using mathematical representations of the virtual camera 60 and projector. The process of translations and rotations (for exchanging camera and projector perspective) may be achieved by corresponding rotation and translation matrices.

Method 400 then proceeds to block 412 which involves projecting the distorted (adjusted) block 410 image using the real projector (e.g. IDU display device 16). From the way the virtual scene is set up, both the virtual camera 60 and real projector are located in the same position and share optical characteristics. When the block 310 screenshot (the adjusted image) is projected on the real projection surface, it appears undistorted and linear (i.e. non-warped) from the visual perspective of the real viewer.

Articulated Robotic Arm

In some embodiments, a robotic positioning system (e.g. pan & tilt mount, spherical wrist, linear actuator(s), articulated robotic arm and/or the like) is provided which may move and/or re-orient IDU display device 16 to change the location of IDU images 18 depending on the location of practitioner 25. One or more of sensors 14 may additionally or alternative be mounted on the robotic arm, so as to mitigate issues which arise due to sensor positioning and/or occlusion. In some embodiments, the robotic positioning system is provided in the form of a series of linear actuators or the like. In other embodiments, the robotic positioning system is provided as a combination of an articulated robotic arm and a series of linear actuators. For brevity, in this description, such a robotic positioning system may be referred to as a robotic arm without loss of generality.

In system 110 of the FIG. 1B embodiment, IDU display device 16A and 3D optical sensors 14A, 14B are mounted at the end of a robotic positioning system 50 which may move and/or re-orient IDU display device 16A and/or 3D optical sensors 14A, 14B. For example, robotic position system 50 may comprise an articulated robotic arm, a series of linear actuators, a combination of an articulated robotic arm and a series of linear actuators, or the like. While not explicitly shown in the block diagram illustration of system 10 in FIG. 1A, IDU display device 16 and 3D optical sensors 14 of system 10 may be mounted at the end of a substantially similar robotic positioning system 50. While not required in system 210 of FIG. 1C, a substantially similar robotic positioning system 50 may be used to house or support additional 3D optical sensor(s) 14—i.e. optical sensors 14 not included in AR headset 40. In some embodiments, other components (e.g. system controller 30) of any of the systems described herein may be mounted or enclosed in suitable enclosures on robotic positioning system 50, although this is not necessary.

Figure 15:
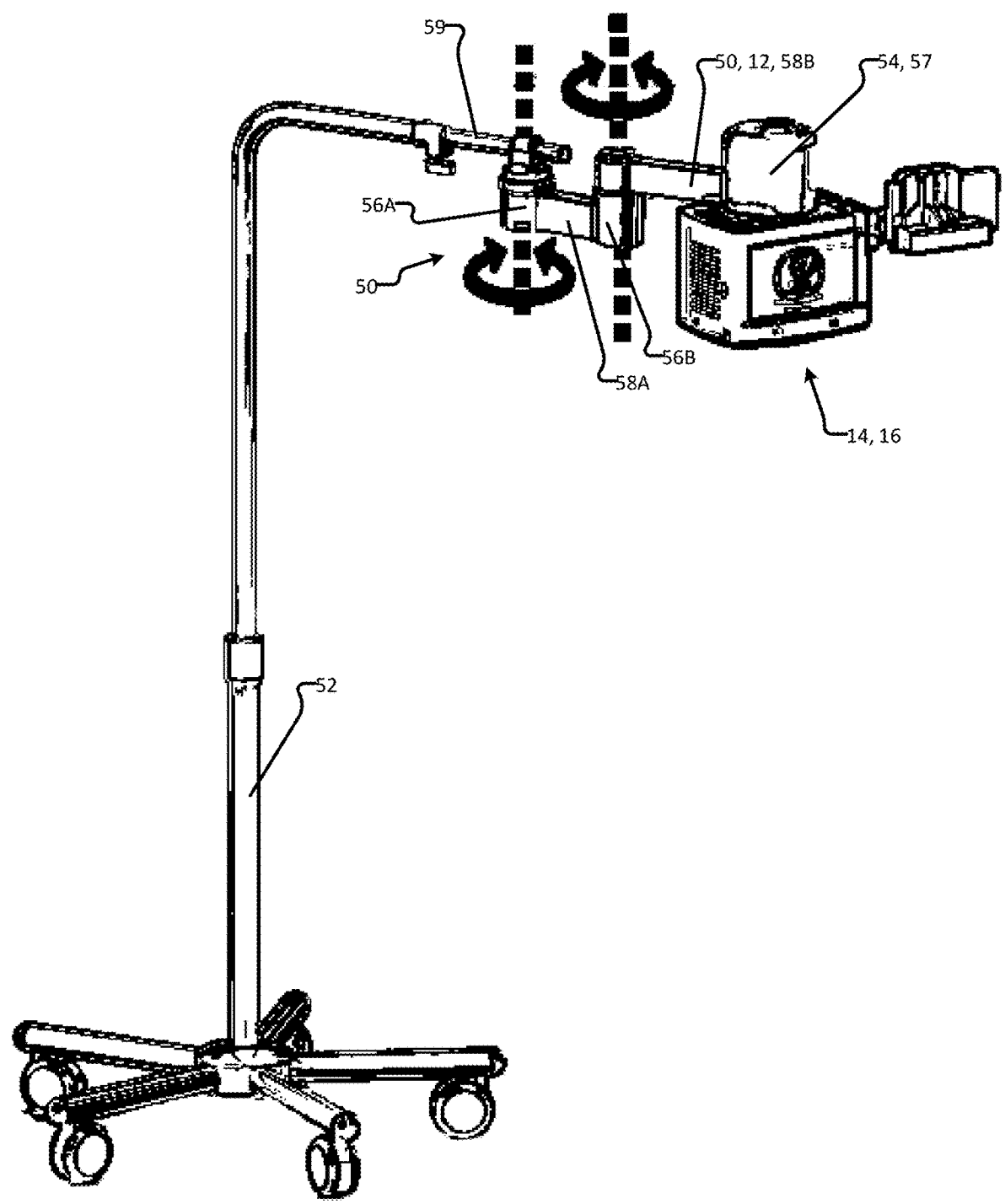
FIG. 15 schematically depicts an articulated robotic arm, according to one embodiment of the invention.

Robotic arm 50 permits the components of any of the systems described herein to be maneuvered using a robotic manipulator. FIG. 15 schematically depicts an articulated robotic arm 50 according to a particular embodiment. Arm 50 of the FIG. 15 embodiment is itself mounted on a rolling stand 52. This is not necessary. In some embodiments, arm 50 may be mounted to a wall, a ceiling or a stationary floor mount. In the illustrated embodiment of FIG. 15, 3D optical sensor 14 and IDU display device 16 are suitably mounted at or near an end 54 of arm 50. Robotic arm 50 may itself be a component of medical equipment 12 which may be controlled using 3D control menus implemented by any of the systems described herein.

Robotic arm 50 allows automatic positioning of the components mounted thereon at suitable locations within the OR 36. For example, robotic arm 50 may permit controllably positioning 3D optical sensors 14 and/or IDU display device 16 at a suitable location over surface 20 of operating table 22. Robotic arm 50 may also be used to retract the components mounted thereon to suitable locations out of the way (e.g. away from operating table 22, away from other medical equipment 12 and/or toward the base of arm 50) when the systems described herein, or the components mounted on arm 50, are not needed or desired during a procedure. This ability to retract may free up space for other surgical equipment.

Robotic arm 50 shown in the FIG. 15 embodiment has two degrees of freedom (2 DOF) about pivot joints 56A, 56B. A motor or other suitable actuator may be mounted to each of pivot joints 56A, 56B to permit pivotal motion of corresponding links 58A, 58B relative to one another and/or relative to mount 59. This illustrated embodiment of robotic arm 50 represents just one of many possibilities. In other embodiments, additional pivot joints and/or translational actuators (e.g. a linear height adjusting actuator) could be incorporated into robotic arm 50. Robotic arm 50 may also comprise one or more additional movable joints 57 which may facilitate motion of the enclosure for IDU display device 16 and 3D optical sensor 14. For example, such moveable joints 57 may permit adjustment of the yaw, pitch and/or roll of IDU display device 16 and/or 3D optical sensor 14.

Robotic arm 50 may permit optical sensors to map all of, or a suitable portion of, OR 36 using 3D optical sensors 14 mounted thereon to determine the locations of people, equipment and/or the like in OR 36. Mapping OR 36 may be useful for a number of reasons. By way of non-limiting example, C-Arm 12B of the FIG. 1B system 110 is a controllable arm which permits movement of medical tools (e.g. medical imaging tools) mounted thereon relative to operating table 22 and patient 24 thereon. However, it can be dangerous or destructive to move C-Arm 12B if the movement path is not clear. Mapping OR 36 using optical sensors 14 mounted to robotic arm 50 (or elsewhere) may be useful to ensure that the movement path of C-Arm 12B is free from obstruction by people or other equipment. In some embodiments, system controller 30 could use 3D optical data obtained from optical sensors 14 mounted on robotic arm 50 or elsewhere to locate and/or identify particular components of medical equipment 12 that may be controlled by the 3D control menus 17 of any of the systems described herein. Such location of medical equipment 12 may be used for head tracking as explained elsewhere herein. Such identification could be made using the shape of the medical equipment 12 and by comparing a library of such shapes to 3D optical data obtained by sensors 14. In some embodiments, system controller 30 could use 3D optical data (e.g. point clouds) obtained from optical sensors 14 mounted on robotic arm 50 or elsewhere to map candidate projection surfaces available within OR 36 to allow (in combination with moveable robotic arm 50) projection of IDU images 18 onto different projection surfaces depending on the location of practitioner 25 within OR 36. For example, if practitioner 25 is proximate to operating table 22, then controller 30 may cause arm 50 to move IDU display projector 16 over operating table 22 and project IDU image 18 onto the surface 20 of operating table 22. However, if practitioner 25 moves closer to a side table (i.e. a different candidate projection surface), then controller 30 may cause arm 50 to move IDU display projector 16 over the side table and to project IDU image 18 onto the surface of the side table.

Head Tracking

As discussed above, it can be desirable in some embodiments to know the location and orientation of head 25B of practitioner 25 (or at least obtain estimates thereof). For example, such practitioner head 25B location and orientation can be used for selection of 3D control menus 17 and corresponding IDU images 18 to be displayed to practitioner 25 (in system 210) and/or for implementing the projection correction methods described herein. In some embodiments, information about the location and/or orientation of the head 25B of practitioner 25 may be ascertained by one or more optical sensors 14 described herein. In some embodiments, the location of the head 25B of practitioner 25 may be ascertained by one or more optical sensors 14 described above and the orientation of the practitioner's head 25B may be estimated from the location. In some embodiments, one or more additional 3D cameras or orientation sensors (e.g. accelerometers, gyroscopes and/or the like) may be used to determine the location and/or orientation of the practitioner's head 25B. In some embodiments, gaze tracking techniques such as those described elsewhere herein may be used to determine information similar to the head orientation.

In some embodiments, one or more 3D optical sensor(s), mounted at appropriate location(s) relative to practitioner 25 may be used to detect the full practitioner head 25B pose—i.e. position and orientation. Such 3D optical sensor(s) may or may not be the same 3D optical sensors 14 used to detect user interactions with 3D control menu 17. In some embodiments, this head pose sensing 3D optical sensor is capable of using modulated infrared light to sense 3D locations for a 2D array of pixels and to form a corresponding point cloud. This point cloud data can then be processed by means of 3D machine vision method(s), whereby the practitioner's head is identified and localized relative to the sensor. A suitable non-limiting example of a machine vision method for identifying head pose is described in N. Ziraknejad, "Driver head pose sensing using a capacitive array and a time-of-flight camera," University of British Columbia, 2014, which is hereby incorporated herein by reference. The head pose sensing 3D optical sensor may be tuned for a detection range of up to several meters. In some embodiments, multiple people located in the range of the head pose sensing 3D optical sensor can be detected and delineated from the background. Additionally, a given person can be tracked and distinguished from other nearby persons within view. In some embodiments, suitable indicia may be used to identify one practitioner for whom 3D control menus 17 are presented. Such indicia can include indicia that can be detected by the head pose sensing 3D optical sensor (e.g. facial recognition indicia, uniquely shaped headwear and/or the like) or such indicia can include other indicia, such as a wearable RFID tag and/or the like.

System controller 30 may be involved in the estimation of head position or the head position may be communicated to system controller 30. System controller 30 may then adjust 3D control menu 17 and/or IDU image 18 for an optimal size and location in front of the desired user (e.g. practitioner 25 described elsewhere herein). In addition, the head position estimate enables system controller 30 to determine a vector from the practitioner's head 25B to the location of the IDU image 18. For example, the vector may be determined by detecting (e.g. by way of one or more optical sensors) Purkinje reflections (i.e. glints) in one or both of the eyes of practitioner 25. This vector may provide a proxy or estimate for the orientation of the practitioner's head 25B. In some embodiments, where IDU display device 16 comprises a projector, the vector from the practitioner's head 25B to the projection surface 20 onto which IDU image 18 is projected can also be calculated. This vector may be used in the projection correction methods described elsewhere herein. An accurate vector leads to an optimally corrected projection of IDU image 18.

In addition or in the alternative, point cloud data may be analyzed to estimate the orientation of the practitioner's head 25B. A 3D machine vision method can detect characteristics of a user's nose, cheeks and/or other facial structures to estimate the orientation of the practitioner's head 25B. One non-limiting example of such a machine vision method is described in N. Ziraknejad, "Driver head pose sensing using a capacitive array and a time-of-flight camera," University of British Columbia, 2014. The orientation of the practitioner's head 25B may be used as a proxy or estimate of the gaze direction of practitioner 25. Based on this process, the orientation of the practitioner's head 25B may be used to estimate the line of sight of practitioner 25 using one or more 3D optical sensors—no wearables are needed for this technique. However, in some embodiments, the one or more 3D optical sensors may be integrated into AR headset 40 of the type described elsewhere herein. In some embodiments, other gaze tracking techniques, such as those described in PCT/CA2008/000987 for example, could be used to directly estimate the line of sight of practitioner 25. Such gaze tracking techniques could be implemented in an AR headset 40 or using separate components suitably mounted in the OR 36. While this description provides a number of exemplary techniques for estimating the line of sight of practitioner 25, it should be understood that any other suitable line-of-sight estimating technique known now or that becomes known in the future could be used in accordance with various embodiments of the invention. Such line-of-sight estimation techniques could be based on data from any suitable types of sensors, including without limitation 2D and 3D optical sensors, orientation sensors in an AR headset, accelerometers, gyroscopes, and/or the like).

As discussed above, line-of-sight information may be matched with the locations of particular components of medical equipment 12 (or locations of their control modules 32) within the OR 36. If the line of sight (i.e. gaze direction) of practitioner 25 is directed to within a threshold spatial region corresponding to a piece of controllable medical equipment 12 (or to its control module 32, or to any location where a 3D control menu 17 has been previously pinned or arbitrarily positioned by practitioner 25), then any of the systems described herein may activate a corresponding 3D control menu 17 and display a corresponding IDU image 18 suitable for controlling that given piece of medical equipment 12. Based on the estimated line-of-sight information and the corresponding component of controllable medical equipment 12 (or the corresponding control module 32), the 3D control menu 17 and corresponding IDU image 18 presented to practitioner 25 may present custom menu items 19 corresponding to the functions of the component of controllable medical equipment 12 that practitioner 25 is looking toward. This may mean a custom 3D control menu 17 and corresponding custom set of menu items 19 and corresponding custom IDU image 18 depending on the component of medical equipment that practitioner 25 is looking toward. As discussed above, control modules 32 corresponding to components of medical equipment 12 and/or the component of medical equipment 12 themselves may comprise physical displays which may act as IDU displays 16 described herein and upon which custom 3D control menus 17 and corresponding custom IDU images 18 may be displayed.

For example, if system controller 30 determines that the line-of-sight of practitioner 25 is oriented toward medical image display 12D (see FIGS. 1B and 1C), then controller 30 may elect to display a specific 3D control menu 17 (which may be specific to controlling medical image display 12D) and a corresponding specific IDU image 18. In some embodiments, a toggle may be provided for each 3D control menu 17 and IDU image 18, so that practitioner 25 may elect whether or not to have such 3D control menu 17 and IDU image 18 presented. In some embodiments, system controller 30 may elect not to display any 3D control menu 17. For example, system controller 30 may elect not to display any 3D control menu 17 when the head 25B of practitioner 25 is oriented toward a body part being operated on.

To simplify this process, certain user line-of-sight (i.e. gaze direction) regions may be defined and utilized to activate corresponding 3D control menus 17. For example, the yaw of the practitioner's head orientation may be predictably calculated within a range of 45°-135°, where 90° is the gaze of practitioner 25 staring directly forward with a direction substantially perpendicular to a long dimension of the operating table 22. This range may then be split into three sections (45°-75°, 75°-105°, 105°-135°) to represent distinct regions for the activation of different 3D control menus 17, which may in turn correspond to different components of medical equipment 12 (or their control modules 32).

Methods for User Detection and Tracking

A first technique for tracking a practitioner 25 (or a portion of the body of a practitioner 25) is described in N. Ziraknejad, "Driver head pose sensing using a capacitive array and a time-of-flight camera," University of British Columbia, 2014. This method is based on the 3D detection of the human nose—a facial feature with distinct curvature characteristics. By first delineating the head of the user, utilizing standard clustering and filtering techniques, a unique HK curvature analysis is performed to localize surface peaks and troughs—pinpointing the tip of the nose and spot between the eyes (at the base of the nose). Post-processing then structures a facial coordinate frame based on these two positions as well as the centroid of the head point cloud. Then, a standard geometric approach enables a comparison of the facial coordinate frame and camera coordinate frame to determine the user's head orientation—notably the pitch and yaw. This method is capable of robustly determining a practitioner's full head pose without the use of special markers or wearable items on the practitioner 25. The practitioner's head orientation vector may be used as an estimate of the practitioner's line-of-sight, as discussed elsewhere herein.

Another example for identifying and tracking a practitioner's head 25B involves the identification of the practitioner's eyes. The eyes are a common feature that can be detected using standard 2D optical sensors. They can be identified by the reflectivity of the eye (e.g. Purkinje reflections or glints), detection of the iris, or by their shape. One or more aligned 3D optical sensors may be used to determine a 3D position for the eyes. If the field-of-view of both 2D and 3D optical sensors are appropriately mapped, generic 2D detection methods for eye detection and a mapping to 3D data could be utilized for practitioner identification and tracking.

Various additional features of the human head can also be detected in order to identify and track the practitioner's head position. Examples of such features include: eyebrow ridge, chin, cheeks, and lips. Each of these features has unique and generalized curvature properties which can be analyzed. Such methods may involve the detection of a combination of a plurality of the above features to provide a robust method for identification and tracking.

Other methods may be used to analyze optical sensor information to identify and track a practitioner's upper body. Some such methods may involve detecting the shape of the practitioner's head, neck, and/or shoulders. In fact, a 2D optical sensor could be utilized for this purpose and aligned with a 3D optical sensor to determine 3D coordinate data—similar to the eye detection example above. However, a well-filtered 3D point cloud is sufficient for this purpose. The typical shape of a human head is known, and can be deciphered from a plethora of point cloud clusters within the field-of-view of the 3D optical sensor. By removing noise and utilizing a Euclidean (or other suitable) clustering method (grouping points in the point cloud based on proximity and density), larger clusters could be evaluated for the outline shapes of a human head, neck, and/or shoulders.

Another example technique which may be used for practitioner identification and tracking based on a 3D point cloud comprises filtering and clustering the point cloud as described in the previous example. The highest cluster could be identified as a practitioner's head. The centroid of this cluster (average position) of points could be calculated to produce a 3D position of the practitioner's viewpoint. An alternative to the centroid calculation is to decipher the point with the greatest Euclidean distance to the edge of the cluster of 3D points.

Methods for User Identification

In a typical OR 36 there will be more than one human. There can be a desire in some embodiments to identify one such human (the control practitioner 25) to be in control of the systems described herein.

In some embodiments, the human closest to 3D optical sensor(s) 14 or closest to some other reference point in OR 36 may be selected to be the control practitioner 25. The 3D positions of every visible human can be compared to the reference point and the human located at the minimum distance to the reference point can be selected to be the control practitioner 25.

In some embodiments, a plurality of audio microphones can be arranged and utilized to identify the control practitioner 25. By listening for a keyword, information from such microphones can use traditional triangulation techniques for localizing the control practitioner 25. Each microphone will sense an input audio magnitude/amplitude. Based on a known configuration of microphones and the magnitude values, the 3D location of the control practitioner 25 can be triangulated. These techniques are referred to as methods for 3D sound localization.

Fiducial markers could be placed on suitable surgical clothing (e.g. on headgear, on the shoulders of surgical scrubs and/or the like) to detect and identify relevant humans within OR 36. Based on differences between such markers, one human in OR 36 could be identified as the control practitioner 25. By way of non-limiting example, such markers could comprise optical (e.g. infrared)-reflective markers, electromagnetic (e.g. RFID) tags and/or other indicators detectable by optical sensor or electromagnetic sensors, placed on the outer surface of surgical clothing so that such markers could be detected by 3D or 2D optical sensor(s). By identifying arrays or specific configurations of such markers, unique users could also be identified in real-time.

In some embodiments, a control practitioner 25 may identify themselves as the control practitioner by carrying out a specific hand gesture—e.g. a wave or finger configuration within view of 3D optical sensor 14. By identifying various 3D point clusters within the scene (or only delineating the closest clusters), points can be analyzed for specific shapes to change control to a new control practitioner 25.

Many methods exist for face detection and identification. Any of the systems described herein could utilize one or more of these facial recognition techniques for not only detecting human faces, but also identifying unique known users in the workspace, including identifying a control practitioner 25. A human face detected by a 2D optical sensor, could be aligned with the 3D optical sensor's output to find control practitioner 25 in 3D. Also, certain users (e.g. surgeons) could be catalogued as authorized control practitioners 25 and certain other users could be catalogued as troubleshoot users (e.g. nurses).

Other sensor-based methods could also be utilized for allowing a particular human to become the control practitioner 25 and to assume control of the system. For example, a low-proximity sensor like a capacitive sensor could sense a human's specific gesture command to identify the control practitioner 25. In such embodiments, it would be desirable for the 3D position of the capacitive sensor relative to the system or 3D optical sensor(s) 14, in this case, to be known to register the control practitioner's 3D position in the system's world coordinate frame. In other embodiments, control practitioner 25 may be identified by way of voice recognition, body scan recognition, retinal scans, and/or the like.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, unless the context dictates otherwise, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Software and other modules may reside on servers, workstations, personal computers, tablet computers, image data encoders, image data decoders, PDAs, color-grading tools, video projectors, audio-visual receivers, displays (such as televisions), digital cinema projectors, media players, and other devices suitable for the purposes described herein. Those skilled in the relevant art will appreciate that aspects of the system can be practiced with other communications, data processing, or computer system configurations, including: Internet appliances, hand-held devices (including personal digital assistants (PDAs)), wearable computers, all manner of cellular or mobile phones, multi-processor systems, microprocessor-based or programmable consumer electronics (e.g., video projectors, audio-visual receivers, displays, such as televisions, and the like), set-top boxes, color-grading tools, network PCs, mini-computers, mainframe computers, and the like.

The invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in whole or in part in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

For example:
- In some embodiments, a first "top level" 3D control menu 17 and a corresponding "top level" IDU image 18 may be presented to practitioner 25. This top level 3D control menu 17 may comprise menu items 19 where each menu item corresponds to a particular one of the various components of controllable medical equipment 12. When a practitioner 25 selects one of the menu items 19 from the top level 3D control menu 17, a sub-3D control menu 17 and corresponding IDU image 18 corresponding to the selected component of medical equipment 12 may be presented to practitioner 25. For example, a top level 3D control menu 17 may allow a practitioner to select between menu items 19 corresponding to a surgical lamp 12A and an operating bed 22. If the practitioner 25 selects the top level menu item 19 corresponding to surgical lamp 12A, then the system may present a sub-3D control menu 17 and corresponding IDU image 18 that is specific to the surgical lamp 12A. This sub-3D control menu 17 may comprise menu items 19, such as brightness level, focus level, light orientation and/or the like, which are specific to controlling surgical lamp 12A.
- In some embodiments, system controller 30 may be configured to be in communication with the control modules 32 of any controllable medical equipment 12 in OR 36. System controller 30 may perform a handshaking routine (upon start-up and/or from time to time) with any such control modules 32 to identify which medical equipment 12 is in OR 36. System controller 30 may adjust one or more control menus 17 (e.g. the "top level" control menu) and/or the one or more corresponding IDU images 18 (e.g. the "top level" IDU image) based on medical equipment 12 that is present or not present in OR 36 based on the outcome of such handshaking procedure.

Control modules 32 are described herein as being able to control medical equipment 12. Unless the context dictates otherwise, the term control should be understood to be broad enough to encompass positioning or configuring positions of such medical equipment. For example, controlling a C-Arm 12B or surgical light 12A should be understood to include positioning the C-Arm 12B using any of the C-Arm's controllable actuators and/or positioning the surgical lamp 12A using any available actuators.

The location and orientation of the practitioner's head 25B and/or the line of sight of the practitioner's gaze can be used to control surgical lamps 12A without independent interaction with 3D control menus 17. For example, system controller 30 may access information (e.g. a vector) based on the location and orientation of the practitioner's head 25B and/or the line of sight of the practitioner's gaze and may control one or more surgical lamps 12A to direct their light toward the location where this vector intersects operating table 22 or some other surface in OR 36.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A system for touchless control of one or more medical equipment devices in an operating room, the system comprising:
    a 3D optical sensor connected for detecting one or more gestures made by a practitioner in a sensing volume of the sensor;
    a controller connected to receive 3D optical data from the 3D optical sensor and configured to provide a three-dimensional control menu, the three-dimensional control menu comprising a plurality of menu items, each menu item selectable by the practitioner by one or more hand gestures made by the practitioner in a volumetric spatial region corresponding to the menu item in the sensing volume; and
    one or more interactive display unit (IDU) displays for displaying, outside of the sensing volume, one or more IDU images corresponding to a current configuration of the three-dimensional control menu, the one or more IDU images providing indicia of any one or more selected menu items;
    wherein the controller is configured to determine selection of any particular one of the menu items and to deliver a corresponding operational command to at least one of the one or more medical equipment devices to control operation of the at least one of the one or more medical equipment devices;
    wherein the one or more medical equipment devices comprise a plurality of medical equipment devices; and
    wherein the controller is configured to:
        provide a first, top level, plurality of menu items, each first, top level, menu item selectable by the practitioner by one or more hand gestures made by the practitioner in a volumetric spatial region corresponding to the first, top level, menu item in the sensing volume and interpret selection of any particular one of the first, top level, menu items by delivering a corresponding operational command to select a corresponding one of the plurality of medical equipment devices; and after selection of any particular one of the first, top level, menu items, provide a second, sub level, plurality of menu items, each second, sub level, menu item corresponding to a specific operational command of the corresponding one of the plurality of medical equipment devices and each second, sub level, menu item selectable by the practitioner by one or more hand gestures made by the practitioner in a volumetric spatial region corresponding to the second, sub level, menu item in the sensing volume, and interpret selection of any particular one of the second, sub level, menu items by delivering a corresponding specific operational command to the corresponding one of the plurality of medical equipment devices.

2. A system according to claim 1 wherein the one or more IDU images displayed outside of the sensing volume comprise, for at least one IDU image, a two-dimensional representation of the three-dimensional control menu.

3. A system according to claim 1 wherein the controller is configured, based on input from one or more sensors, to estimate at least one of a location of a head of the practitioner and an orientation of the head of the practitioner and to adjust the display of the one or more IDU images by the one or more IDU displays based at least in part on the at least one of the estimated location of the head of the practitioner and the estimated orientation of the head of the practitioner.

4. A system according to claim 3 wherein the controller is configured to adjust the display of the one or more IDU images based at least in part on the at least one of the estimated location of the head of the practitioner and the estimated orientation of the head of the practitioner by adjusting at least one of: a location, outside of the sensing volume, at which the one or more IDU images are displayed; and an orientation of the one or more displayed IDU images.

5. A system according to claim 3 wherein the controller is configured to adjust the display of the one or more IDU images based at least in part on the at least one of the estimated location of the head of the practitioner and the estimated orientation of the head of the practitioner by adjusting one or more physical displays on which the one or more IDU images are displayed.

6. A system according to claim 3 wherein the one or more IDU displays are configured to display the one or more IDU images by projecting the IDU image onto a projection surface.

7. A system according to claim 6 wherein the controller is configured to adjust the one or more IDU images based at least in part on the at least one of the estimated location of the head of the practitioner and the orientation of the head of the practitioner by modifying the projection surface on which the one or more IDU images are projected.

8. A system according to claim 3 wherein the controller is configured to estimate the head orientation of the practitioner based on the estimated head location of the practitioner.

9. A system according to claim 1 wherein the controller is further configured, based on input from one or more sensors, to estimate a line of sight of a practitioner.

10. A system according to claim 1 comprising an augmented reality headset worn by the practitioner, wherein the one or more IDU displays are configured to display the one or more IDU images corresponding to the three-dimensional control menu by displaying one or more corresponding virtual IDU images to the practitioner by projecting the one or more IDU image from the augmented reality headset into one or both of the eyes of the practitioner.

11. A system according to claim 1 wherein a first IDU display is configured to display, in a first location outside of the sensing volume, a first device-specific IDU image by displaying the first device-specific IDU image on a first physical display outside of the sensing volume, the first physical display being at least one of: part of a first medical equipment device; part of a first control module connected to provide operational commands to the first medical equipment device.

12. A system according to claim 1 wherein the controller is configured to identify the practitioner from among one or more other humans in the operating room to be a controlling practitioner, wherein identifying the practitioner to be the controlling practitioner comprises at least one of: determining that the practitioner is the closest human to a reference location; identifying one or more fiducial markers associated with the practitioner; performing a facial recognition method on the practitioner; identifying one or more gestures performed by the practitioner; performing a voice recognition method on the practitioner; performing a body shape recognition method on the practitioner; and performing a retinal scan on the practitioner.

13. A system according to claim 1 wherein the at least one of the one or more medical equipment devices comprises a medical image display device for displaying medical images of a patient and wherein the corresponding operational command comprises a command which causes the medical image display device to perform one or more of: changing a medical image displayed on the medical image display device and changing characteristics of a medical image displayed on the medical image display device.

14. A system according to claim 1 wherein the one or more IDU images comprise medical image data corresponding to a patient.

15. A system for touchless control of one or more medical equipment devices in an operating room, the system comprising:

a 3D optical sensor connected for detecting one or more gestures made by a practitioner in a sensing volume of the sensor;

a controller connected to receive 3D optical data from the 3D optical sensor and configured to provide a three-dimensional control menu, the three-dimensional control menu comprising a plurality of menu items, each menu item selectable by the practitioner by one or more hand gestures made by the practitioner in a volumetric spatial region corresponding to the menu item in the sensing volume; and one or more interactive display unit (IDU) displays for displaying, outside of the sensing volume, one or more IDU images corresponding to a current configuration of the three-dimensional control menu, the one or more IDU images providing indicia of any one or more selected menu items;

wherein the controller is configured to determine selection of any particular one of the menu items and to deliver a corresponding operational command to at least one of the one or more medical equipment devices to control operation of the at least one of the one or more medical equipment devices;

wherein the controller is further configured, based on input from one or more sensors, to estimate a line of sight of a practitioner; and wherein, when the estimated line of sight is directed within a first spatial range around a first medical equipment device, the controller is configured to determine that the practitioner is looking at the first medical equipment device and wherein, after determining that the practitioner is looking at the first medical equipment device, the controller is configured to provide a first device-specific three-dimensional control menu comprising first device-specific menu items which, when selected, result in delivering corresponding operational commands to the first medical equipment device to control operation of the first medical equipment device; and wherein, after determining that the practitioner is looking at the first medical equipment device, the controller is further configured to cause a first IDU display from among the one or more IDU displays to display, in a first location outside of the sensing volume, a first device-specific IDU image comprising graphics or text corresponding to the first device-specific menu items.

16. A system according to claim 15 wherein the controller is configured to estimate the line of sight of the practitioner by estimating a location and orientation of a head of the practitioner and estimating the line of sight of the practitioner to be along a line of sight vector, a start of the line of sight vector based on the estimated location of the head of the practitioner and an orientation of the line of sight vector based on the estimated orientation of the head of the practitioner.

17. A system according to claim 16 wherein the controller is configured to estimate the location and orientation of the head of the practitioner based at least in part on data obtained from at least one of: one or more 2D optical sensors; and one or more 3D optical sensors.

18. A system according to claim 15 where, when the estimated line of sight is directed within a second spatial range around a second medical equipment device which is different from the first medical equipment device, the controller is configured to determine that the practitioner is looking at the second medical equipment device and wherein, after determining that the practitioner is looking at the second medical equipment device, the controller is configured to:
provide a second device-specific three-dimensional control menu comprising second device-specific menu items different from the first device-specific menu items which, when selected, result in delivering corresponding operational commands to the second medical equipment device to control operation of the second medical equipment device; and
cause a second IDU display from among the one or more IDU displays to display, in a second location outside of the sensing volume, a second device-specific IDU image comprising graphics or text corresponding to the second device-specific menu items.

19. A system according to claim 15 wherein the at least one of the one or more medical equipment devices comprises a medical image display device for displaying medical images of a patient and wherein the corresponding operational command comprises a command which causes the medical image display device to perform one or more of: changing a medical image displayed on the medical image display device and changing characteristics of a medical image displayed on the medical image display device.

20. A system according to claim 15 wherein the one or more IDU images comprise medical image data corresponding to a patient.

21. A system for touchless control of one or more medical equipment devices in an operating room, the system comprising:
a 3D optical sensor connected for detecting one or more gestures made by a practitioner in a sensing volume of the sensor;
a controller connected to receive 3D optical data from the 3D optical sensor and configured to provide a three-dimensional control menu, the three-dimensional control menu comprising a plurality of menu items, each menu item selectable by the practitioner by one or more hand gestures made by the practitioner in a volumetric spatial region corresponding to the menu item in the sensing volume; and
one or more interactive display unit (IDU) displays for displaying, outside of the sensing volume, one or more IDU images corresponding to a current configuration of the three-dimensional control menu, the one or more IDU images providing indicia of any one or more selected menu items;
wherein the controller is configured to determine selection of any particular one of the menu items and to deliver a corresponding operational command to at least one of the one or more medical equipment devices to control operation of the at least one of the one or more medical equipment devices;
wherein the 3D optical sensor is mounted on a robotic positioning system for at least one of moving or orienting the 3D optical sensor, wherein the 3D optical sensor is configured to capture 3D optical data corresponding to a region of interest in the operation room and wherein the controller is configured to process the captured 3D optical data to locate and identify the one or more medical equipment devices in the operation room that are controllable using the three-dimensional control menu;
wherein the controller is configured to process the captured 3D optical data to locate and identify a particular medical equipment device that is controllable using the three-dimensional control menu;
wherein the controller is configured to provide the three-dimensional control menu by providing a particular device-specific three-dimensional control menu comprising particular device-specific menu items which, when selected, result in delivering corresponding operational commands to the particular medical equipment device to control operation of the particular medical equipment device; and
wherein the IDU display is configured to display the IDU image corresponding to the three-dimensional control menu by displaying a particular device-specific IDU image comprising graphics or text corresponding to the particular device-specific menu items.

22. A system according to claim 21 wherein the robotic positioning system comprises at least one of: an articulated robotic arm; and a series of linear actuators.

23. A system according to claim 21 wherein the robotic positioning system has two or more degrees of freedom.

24. A system according to claim 21 wherein the at least one of the one or more medical equipment devices comprises a medical image display device for displaying medical images of a patient and wherein the corresponding operational command comprises a command which causes the medical image display device to perform one or more of: changing a medical image displayed on the medical image display device and changing characteristics of a medical image displayed on the medical image display device.

25. A system according to claim 21 wherein the one or more IDU images comprise medical image data corresponding to a patient.

\* \* \* \* \*